United States Patent
Chung et al.

(10) Patent No.: US 10,086,083 B2
(45) Date of Patent: Oct. 2, 2018

(54) POLYOL-BASED OSMOTIC POLYDIXYLITOL POLYMER GENE TRANSPORTER AND USE THEREOF

(71) Applicant: SEOUL NATIONAL UNIVERSITY R&DB FOUNDATION, Seoul (KR)

(72) Inventors: Jong Hoon Chung, Seoul (KR); Pankaj Garg, Seoul (KR); Shambhavi Pandey, Seoul (KR); Pill Hoon Choung, Seoul (KR); Chong Su Cho, Seoul (KR); Bog Hee Kim, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 15/523,338

(22) PCT Filed: Oct. 29, 2015

(86) PCT No.: PCT/KR2015/011494
§ 371 (c)(1),
(2) Date: Apr. 28, 2017

(87) PCT Pub. No.: WO2016/068617
PCT Pub. Date: May 6, 2016

(65) Prior Publication Data
US 2017/0246309 A1    Aug. 31, 2017

(30) Foreign Application Priority Data
Oct. 30, 2014 (KR) .......... 10-2014-0149439

(51) Int. Cl.
| | | |
|---|---|---|
| C12N 15/11 | (2006.01) | |
| A61K 9/00 | (2006.01) | |
| A61K 31/7088 | (2006.01) | |
| C08G 73/02 | (2006.01) | |
| A61K 47/48 | (2006.01) | |
| C12N 15/113 | (2010.01) | |
| A61K 48/00 | (2006.01) | |

(52) U.S. Cl.
CPC ........ *A61K 47/48192* (2013.01); *A61K 9/007* (2013.01); *A61K 9/0019* (2013.01); *A61K 31/7088* (2013.01); *A61K 47/48084* (2013.01); *C08G 73/024* (2013.01); *C12N 15/1137* (2013.01); *A61K 48/00* (2013.01); *C12N 2310/14* (2013.01); *C12N 2320/32* (2013.01)

(58) Field of Classification Search
None
See application file for complete search history.

(56) References Cited

FOREIGN PATENT DOCUMENTS

| EP | 2623117 A1 | 8/2013 |
|---|---|---|
| KR | 102007-0059171 A | 6/2007 |
| KR | 10-1239492 B1 | 3/2013 |
| KR | 10-2014-0043962 A | 4/2014 |

OTHER PUBLICATIONS

Won-Seok Lee et al., "Polyxylitol-based gene carrier improves the efficiency of gene transfer through enhanced endosomal osmolysis," Nanomedicine, Nanotechnology, Biology, and Medicine, vol. 10, No. 3, pp. 525-534, Oct. 30, 2013.
Mohammad Ariful Islam et al., "Major degradable polycations as carriers for DNA and siRNA," J. of Controlled Release, vol. 193, pp. 74-89, Jun. 3, 2014.

*Primary Examiner* — Addison D Ault
(74) *Attorney, Agent, or Firm* — Gavrilovich, Dodd & Lindsey LLP

(57) ABSTRACT

The present invention relates to polydixylitol polymer based gene transporter (PdXYP) and a preparation method thereof. Further, the present invention relates to a nucleic acid delivery complex where the nucleic acids for treatment are conjugated to the gene transporter and a pharmaceutical composition for gene therapy including the complex as an active ingredient. In addition, the present invention relates to the gene transporter, gene delivery complex, and gene therapy using the gene transporter and gene delivery complex. It was confirmed that the PdXYP of the present invention has a considerably higher nucleic acid delivery rate than existing gene transporters, has almost no cytotoxicity in the conjugate when conjugated with DNA, also has very high in vivo transfection efficiency, and above all, especially has considerably high transfection efficiency for brain tissues, which has involved difficulty in gene therapy due to the blood brain barrier for a while. Accordingly, the gene transporter of the present invention can not only be used as experimental gene transporters, but can also be broadly used for various tissues in the body based on the nucleic acids for treatment to be conjugated in the field of gene therapy regarding various diseases.

18 Claims, 24 Drawing Sheets

FIG. 1A-C

TEER Values

|  | Before treatment | After treatment |
|---|---|---|
| Control | 199.76±4.9 | 197.12±4.7 |
| PdXYP/DNA | 185.35±3.8 | 183.03±1.7 |

FIG. 12A-C

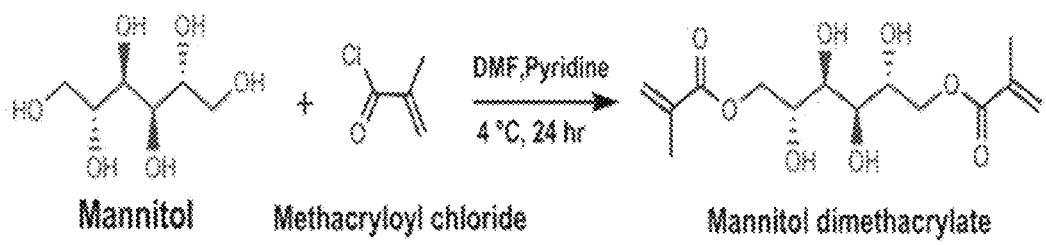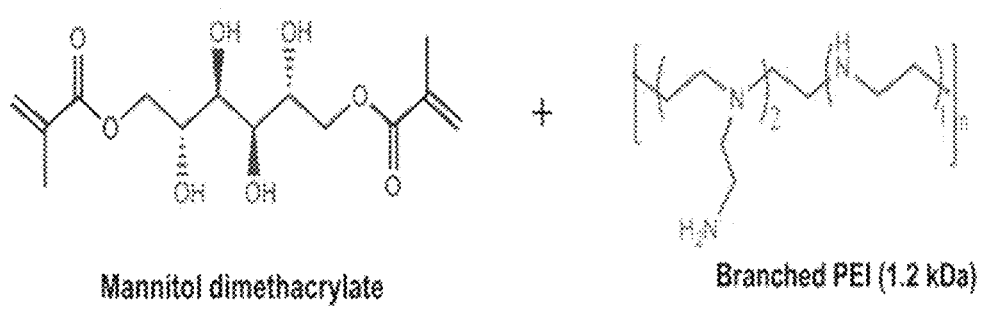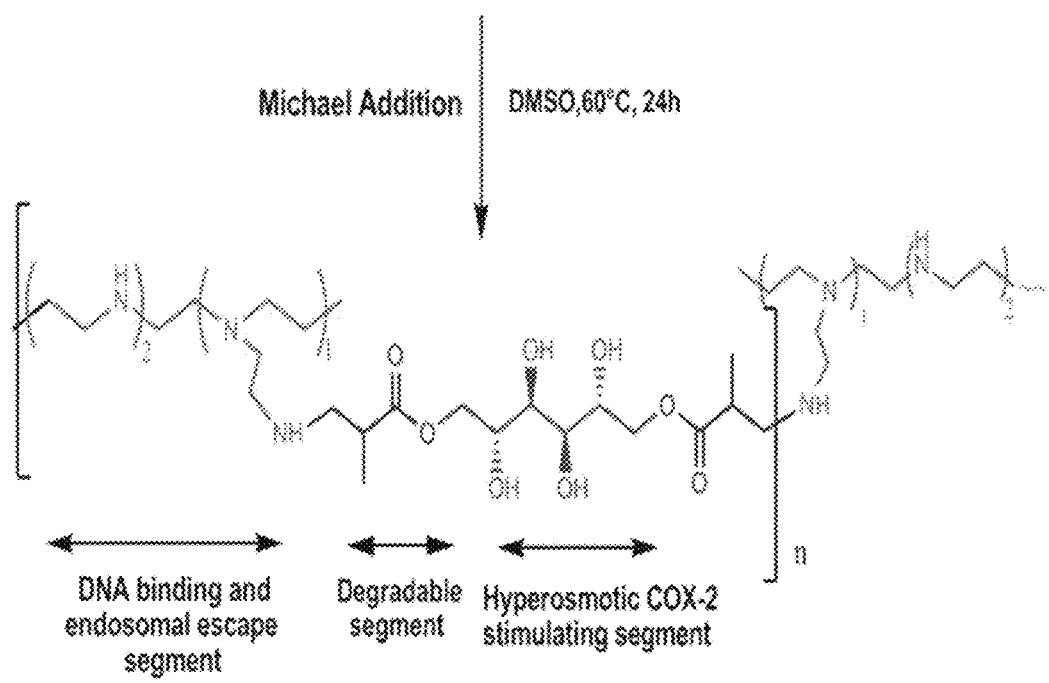
FIG. 13

POLYOL-BASED OSMOTIC POLYDIXYLITOL POLYMER GENE TRANSPORTER AND USE THEREOF

CROSS REFERENCE TO RELATED APPLICATIONS

This application is a U.S. National Stage Application filed under 35 U.S.C. § 371 and claims priority to International application No. PCT/KR2015/011494, filed Oct. 29, 2015, which claims priority to Korean Application No. 10-2014-0149439, filed Oct. 30, 2014, the disclosure of which are incorporated herein by reference.

TECHNICAL FIELD

The present invention relates to a polydixylitol polymer based gene transporter (PdXYP) and a preparation method thereof. Further, the present invention relates to a nucleic acid delivery complex in which nucleic acids for treatment are conjugated to the gene transporter and a pharmaceutical composition for gene therapy including the corresponding complex as an active ingredient. In addition, the present invention relates to the gene transporter, the gene delivery complex, and gene therapy using the gene transporter or the gene delivery complex.

BACKGROUND ART

Gene therapy, which refers to treating diseases by delivering nucleic acids for treatment to desired organs in the body and expressing new proteins in cells, is a method that does not treat symptoms of diseases but treats the causes of diseases and removing the diseases. Gene therapy can have excellent selectivity compared to the general treatments by drugs, and can be applied for a long time by improving cure rates and treatment pace of the diseases that are difficult to be controlled by other treatment methods. As nucleic acids for treatment, DNA is vulnerable to hydrolysis caused by in vivo enzymes and has low efficiency in entering the cells, and therefore, it is necessary to develop a gene carrier that can safely deliver nucleic acids to desired target cells to achieve high expression efficiency for an effective gene therapy.

A gene transporter should have low or no toxicity and be able to deliver genes to desired cells selectively and effectively. These gene carriers are largely classified into viral and non-viral ones. Until recently, for clinical trials, viral vectors that have high transfection efficiency have been used as a gene carrier. However, viral vectors, such as retrovirus, adenovirus, and adeno-associated virus, not only have complex preparation steps, but also have safety problems, such as immunogenicity, infection risk, induction of inflammation, insertion of non-specific DNA, etc., and the problem in that the acceptable DNA size is limited. Therefore, the viral vectors have limitations to be applied in the body. As such, at present, non-viral vectors have gained attention as a replacement for viral vectors.

Non-viral vectors have advantages, such as repeated administrations with minimal immune response, enabling specific delivery to particular cells, excellent storage stability, and easy mass production. Examples of these non-viral vectors may include cationic liposomes, such as N-[1-(2,3-dioleyloxy)-propyl]-N,N,N-trimethyl ammonium chloride (DOTMA), alkylammonium, cationic cholesterol derivatives, gramicidin, etc.

Lately, there has been increasing attention since cationic polymers among non-viral vectors can form a complex through an ionic bond with anionic DNA. Such cationic polymers include poly-L-lysine (PLL), poly (4-hydroxy-L-proline ester), polyethylenimine (PEI), poly-[α-(4-aminobutyl)-L-glycolic acid], polyamidoamine dendrimer, poly-[N,N'-(dimethylamino)-ethyl]-methacrylate (PDMAEMA), etc., and these polymers compress DNA and form nanoparticles to protect DNA from degradation by enzymes and help to invade into cells rapidly and escape from endosomes. Most non-viral vectors have advantages, such as biodegradability, low toxicity, non-immunogenicity, convenience for use, etc., but have problems, such as relatively low transfection efficiency, limited particle size, etc.

Specifically, although most cationic polymers used as non-viral vectors show high transfection efficiency in vitro, which is an environment with low blood serum concentration, the transfection efficiency of the cationic polymer/gene complex is considerably inhibited by various factors present in the blood serum in vivo, thereby making gene entry into cells difficult. This is because non-specific interactions with plasma proteins and blood compositions are induced by an excessive positive electric charge caused on the surface of the cationic polymer/gene complex in vivo. Therefore, the transfection efficiency of cationic polymers is considerably decreased in vivo where a lot of blood serum is present, but not in vitro, where serum-free media or very low concentration of blood serum is present. When this is applied in vivo as it is, aggregates and accumulations in the lung, liver, and spleen, and furthermore opsonization and removal by reticuloendothelial system may be caused. Therefore, it is inevitable to limit the medical applications of the cationic polymers. The PEI, which has been most broadly studied as a non-viral vector, also has considerably low in vivo transfection efficiency and has a problem such as high cytotoxicity and low effects on gene expression due to low blood compatibility. Therefore, there is a need for developing the gene carrier that can enhance transfection efficiency while maintaining the advantages of the existing non-viral vectors.

In particular, the most challenging task in increasing the cure rate by gene therapy was on how to increase the delivery rate of the nucleic acids for treatment that cross biological barriers such as cell membranes, tumor tissues, and the blood brain barrier (BBB). Although various gene therapy targets have been discovered due to recent research on brain diseases, the effects are difficult to be proven because of a lack of means to effectively apply the gene therapy targets to animal models.

Specifically, the BBB, which is a cerebrovascular structure that limits the delivery of substances from the blood to brain tissues, is known to be formed mostly by tight junctions of cerebral capillary endothelium, known to surround blood vessels, and have impermeability to giant molecules such as nucleic acids. Particularly, fat-soluble substances are known to traverse the BBB, but non fat-soluble substances including polar substances, strong electrolytes, etc., are not really known to transmigrate the BBB. Although there is an advantage in that the brain tissues are protected from harmful substances by the BBB, there is a disadvantage in that the accessibility to treatment substances is decreased compared to other tissues in the body by blocking the delivery of radioisotopes, dyes, drugs, etc., required for the treatment of the brain tissues. Under the circumstance where even the delivery of polar compounds to brain tissues through the BBB is not easy, the delivery of nucleic acids, which are large molecules with strong polarity, is even more difficult. Besides the BBB, biologically-hindering mechanisms, such as decomposition by nuclease, immune clearance, difficulty in cell influx, off-target deposition in vivo, etc., make the gene delivery to the brain tissues difficult. Therefore, there is a need for developing a gene transporter that can overcome the hindering mechanisms and perform effective gene therapy for the brain tissues.

Because the gene delivery using most viral vectors is not able to cross the BBB by systemic delivery, direct injection/insertion into the brain is generally performed. However, there are problems where transfection has limited insertion sites and direct injection method is non-invasive for brain tissues. As such, in order to increase the delivery efficiency of substances to brain tissues by systemic delivery, there has been an attempt to increase permeability of the BBB by an intra-arterial injection of an osmotic agent such as mannitol. Specifically, the tissues were pretreated with hyperosmotic mannitol to loosen the tight junctions between the cells, followed by the treatment of various gene/drug delivery vehicles. However, the effect of mannitol was temporary and disappeared after 30 minutes, and the effect disappeared even before the influx of drugs or DNA. Further, the systemic delivery of mannitol has brought an effect of an overall increase of permeability to the BBB and thus it was not possible to specifically increase the permeability of particular substances for delivery.

Even if the genes have transmigrated the BBB, they still have to safely go through with cellular uptake and endosomal trapping to be transported to the cells. Therefore, the procedure for delivering genes to target cells of tissues is the biggest obstacle and technical problem to be solved, in terms of gene therapy for animals.

The present inventors have developed novel gene transporters, and suggested transporters capable of binding to nucleic acids based on mannitol and sorbitol and delivering the nucleic acids into the cells. However, in the field of gene transporters, there is yet a continuous demand for developing gene transporters that have higher delivery efficiency and can effectively deliver the nucleic acids to specific tissues.

DISCLOSURE OF INVENTION

Technical Problem

The present inventors have made extensive efforts to develop a gene transporter that shows low cytotoxicity and high transfection efficiency. As a result, they have found that the polydixylitol polymer (PdXYP), which is a polyol-based osmotic gene transporter prepared by conjugating polyethylenimine (PEI) with dixylitol diacrylate, shows very low cytotoxicity and considerably high transfection efficiency by the high transmigration rate across the BBB due to a xylitol dimer backbone, increased membrane permeability rate by osmotic activity, and proton sponge effect by stimulated intracellular uptake and the PEI backbone. They have confirmed that the polyol-based osmotic gene transporter can be effectively used as a gene transporter for gene therapy, thus completing the present invention.

Technical Solution

It is an object of the present invention to provide a polydixylitol polymer-based gene transporter (PdXYP), which has considerably increased transfection efficiency as a gene transporter, without showing cytotoxicity.

It is another object of the present invention to provide a method for preparing the PdXYP.

It is still another object of the present invention to provide a nucleic acid delivery complex in which the PdXYP is conjugated with nucleic acids for treatment.

It is still another object of the present invention to provide a pharmaceutical composition for gene therapy containing the nucleic acid delivery complex as an active ingredient.

Advantageous Effects

The present inventors have confirmed that the PdXYP of the present invention has a considerably higher nucleic acid delivery efficiency than existing gene transporters, has almost no cytotoxicity of the conjugate when conjugated with DNA, also has very high transfection efficiency in vivo, and above all, especially has considerably high transfection efficiency for brain tissues, which had been experiencing difficulty in gene therapy due to the blood brain barrier in the past. Accordingly, the gene transporter of the present invention can not only be used as experimental gene transporters, but can also be broadly used for various tissues in the body based on the conjugated nucleic acids in the field of gene therapy with respect to various diseases.

BRIEF DESCRIPTION OF DRAWINGS

FIG. 8b shows the result of spectrofluorometrical analysis of media, which were respectively obtained from upper and lower chambers of the BBB after treating with fluorescent (FAM)-labeled pDNA (pGL3), a PdXYP-pGL3 nanoplex, and PEI-pGL3 in the upper chamber of the BBB followed by incubation.

FIG. 9a shows luciferase expression level by in vivo bioimaging after administering the PdXYP/pDNA polyplex, the PEI/pDNA polyplex, and the naked pGL3 DNA to mice.

FIG. 13 shows a schematic diagram of a method for preparing a polymannitol based gene transporter (PMGT) that has a structure similar to that disclosed in Korean Patent Application Publication No. 10-2014-0043962.

BEST MODE FOR CARRYING OUT THE INVENTION

In an aspect to achieve the above objects, the present invention provides a polydixylitol polymer based gene transporter (PdXYP) represented by the following Formula 1.

[Formula 1]

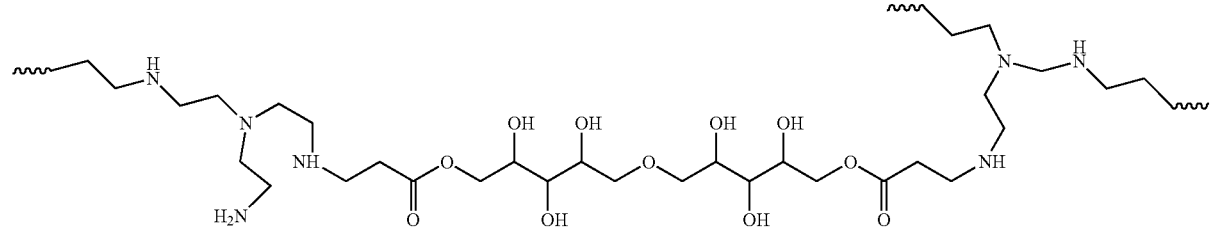

Figure 1:
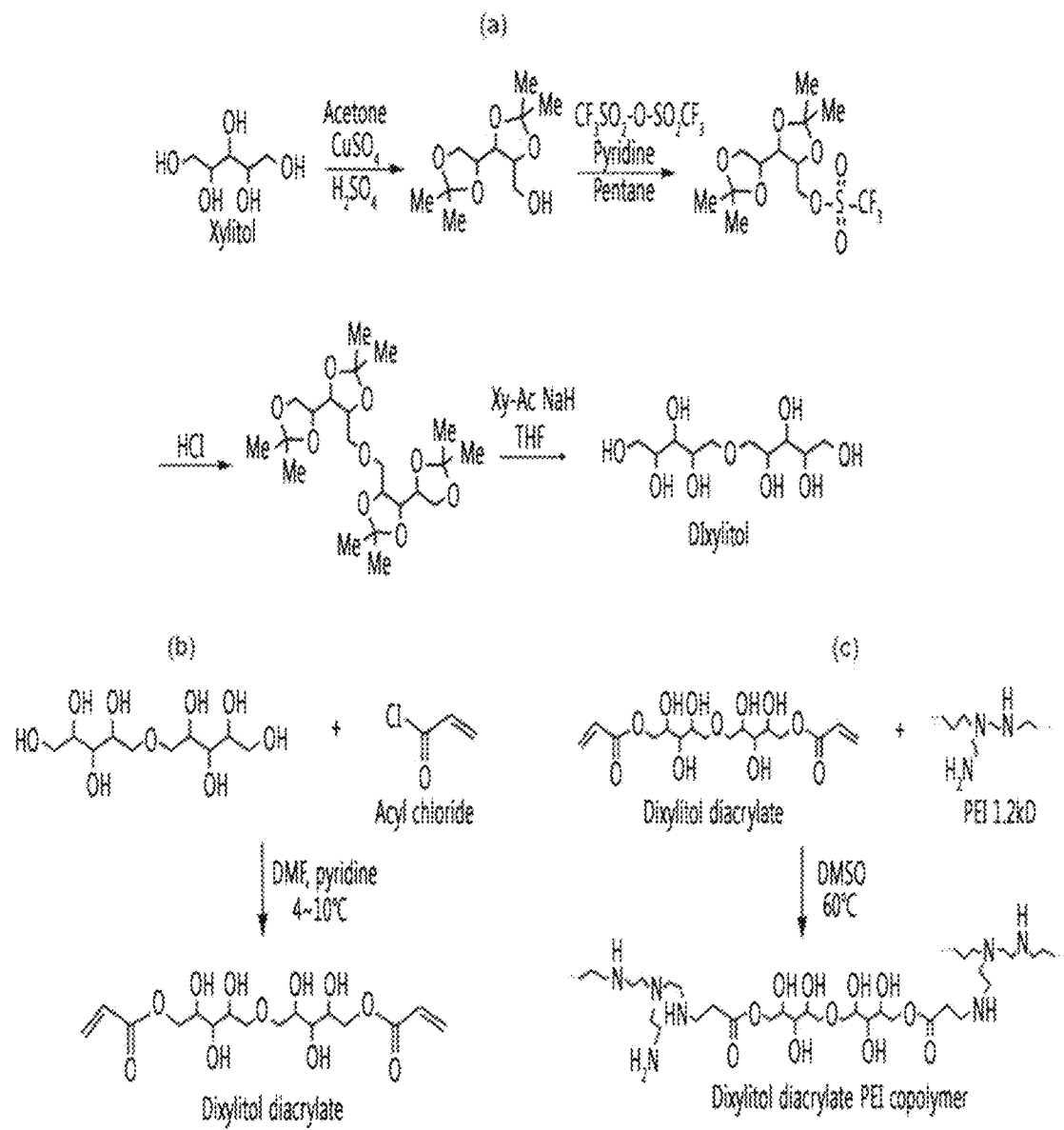
FIG. 1A-C shows a procedure for synthesizing the PdXYP of the present invention.

The polydixylitol polymer based gene transporter (PdXYP) according to the present invention may be prepared by a method including: preparing dixylitol by acetone/xylitol condensation, preparing dXYA by esterifying the dixylitol with acryloyl chloride, and performing a Michael addition reaction between dXYA and low molecular weight-PEI (FIG. 1).

As used herein, the term "xylitol" refers to a sugar alcohol based-natural sweetener having a formula of $C_5H_{12}O_5$. Xylitol can be extracted from birch trees, oak trees, etc., and has a unique pentose structure. In the present invention, dixylitol, which is a xylitol dimer, is used to prepare the PdXYP of the present invention.

As used herein, the term "acryloyl chloride" may be also called 2-propenoyl chloride or acrylic acid chloride. The compound has the properties of producing acrylic acid by reacting with water, forming an anhydride by reacting with sodium carboxylate, or forming an ester group by reacting with alcohol. In an exemplary embodiment of the present invention, dixylitol, the dimer of xylitol, which is sugar alcohol-based, was reacted with acryloyl chloride and esterified to form dXYA.

As used herein, the term "polyethylenimine (PEI)", which is a cationic polymer that has primary, secondary, and tertiary amino groups, has a molar mass ranging from 1,000 g/mol to 100,000 g/mol, effectively compresses anionic nucleic acids into colloidal particles, and has high gene delivery efficiency due to the buffering capacity of pH reactivity, thereby effectively delivering genes to various cells in vivo and in vitro. In the present invention, PEI may be in a linear form as represented by the following Formula 2 or a branched-type as represented by the following Formula 3, and PEI has a low molecular weight, specifically ranging from 50 Da to 10,000 Da, considering cytotoxicity (based on the weight-average molecular weight). PEI is dissolved in water, alcohol, glycol, dimethylformamide, tetrahydrofuran, esters, etc., but is not dissolved in high molecular weight hydrocarbons, oleic acid, and diethyl ether.

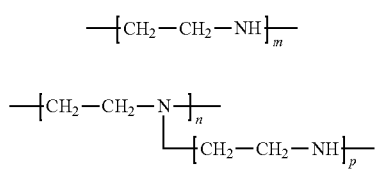

[Formula 2]

[Formula 3]

In the present invention, polyethylenimine (PEI) and dixylitol diacrylate (dXYA) form the PdXYP of the present invention through Michael addition reaction. By including cationic PEI as a part, the PdXYP of the present invention may induce an aggregation of anionic nucleic acids. In particular, there has been a continuous demand for gene carrier, which has lower cytotoxicity and higher transfection efficiency, compared to PEI that has been already known as a gene transporter or polyesteramine that may have been synthesized therefrom. Specifically, there has been a continuous demand for the gene transporter, which enhanced the transmigration rate of the BBB that has been considered as obstacles for gene therapy in brain tissues for a while.

The PdXYP of the present invention may transmigrate the BBB at high efficiency. In an exemplary embodiment of the present invention, the gene transporter in which the PdXYP of the present invention was conjugated with luciferase-expressing vector as a reporter gene was prepared. As the result of confirming this by an in vitro BBB model and an in vivo luciferase-expressing bioimaging experiment, significant luciferase expression in brain tissues was confirmed by traversing the barrier without damaging the blood barrier when the PdXYP of the present invention was used, compared to the case where other gene transporter (PEI) was used. Throughout the experiment, it was confirmed that when the PdXYP of the present invention was used as a gene transporter, the in vivo gene delivery efficiency was not only more remarkable compared to other gene transporters, but was also able to effectively deliver genes to brain tissues that had very low delivery efficiency when existing gene transporters were used.

In particular, the gene transporter of the present invention may be the PdXYP, which is another name for the VB-PdXYP in which the PdXYP is further connected by vitamin B6. The PdXYP, which is further connected by the vitamin B6, may have the structure of the following formula 4.

In the present invention, "vitamin B6" is present as pyridoxine (PN), pyridoxal (PL), pyridoxamine (PM), or a phosphorylated form (PNP, PLP, and PMP) of each of the above and used as coenzymes of many bioactive enzymes. Specifically, when used as coenzymes, they are used in the forms of PLP and PMP. PLP is known as a form with very high biological activity. The active vitamin B6 of the present invention (pyridoxal 5'phosphate (PLP)) may have a structure of the following Formula 5.

Formula 5

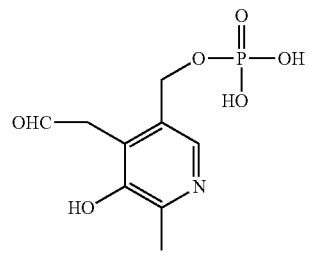

Figure 2:
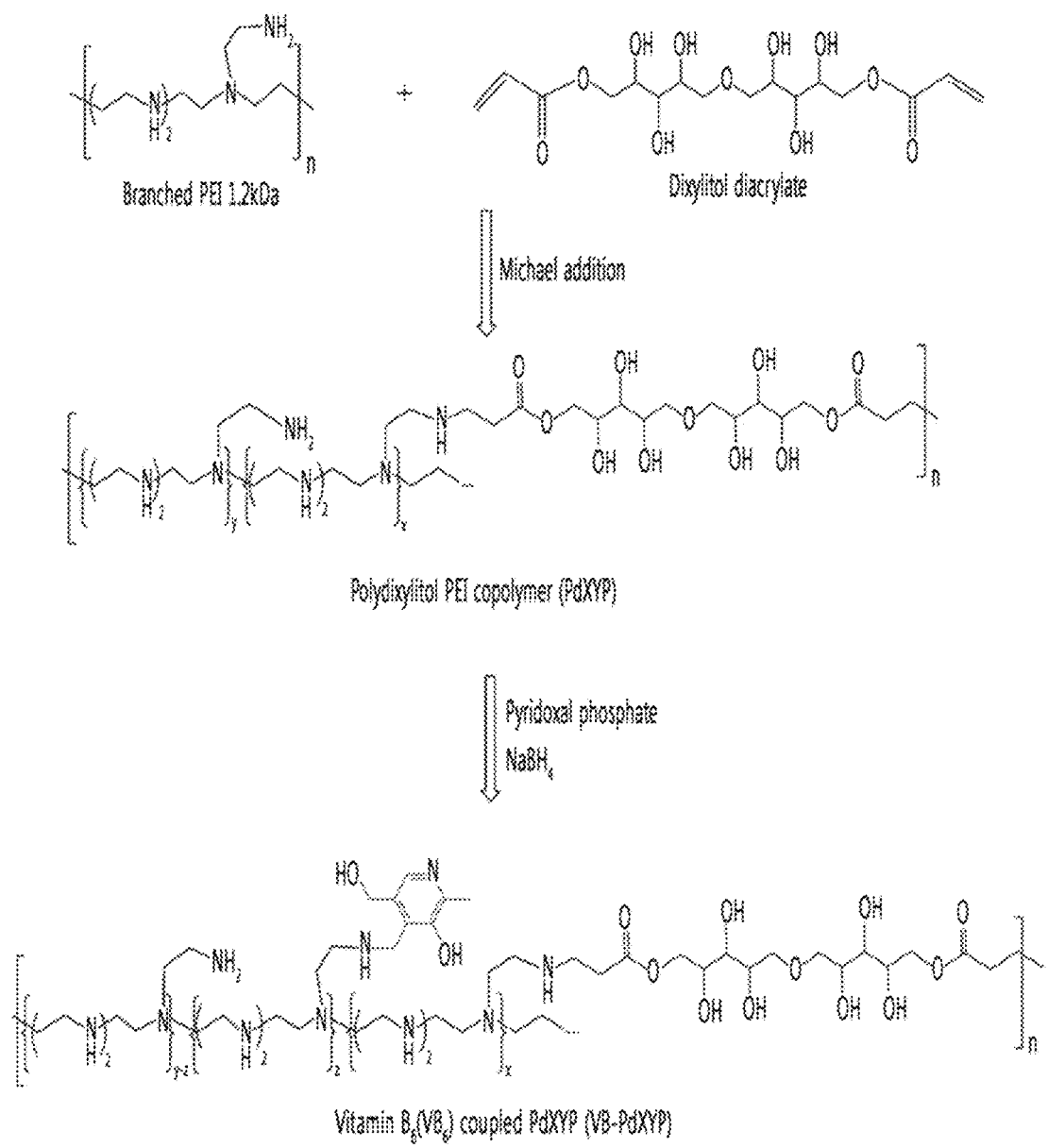
FIG. 2 shows a procedure for synthesizing the VB-PdXYP of the present invention.

In the present invention, the pyridoxal 5'phophate (PLP) and the prepared PdXYP were reacted to form transient Schiff base, which was then reduced to obtain the VB-PdXYP using NaCNBH4 (FIG. 2).

The VB-PdXYP of the present invention binds to vitamin B6 translocator, which is present in a cell membrane due to the vitamin B6 and induces the adhesion of the transporter to the cell membrane. After being bound to the cell membrane, an intracellular influx of nucleic acids is effectively induced by proton sponge effect due to the PdXYP and therefore, considerably improved transfection efficiency may be exhibited. In addition, due to very low cytotoxicity, the VB-PdXYP may be effectively used as a gene transporter for gene therapy. Specifically, the VB-PdXYP may show high transfection efficiency in cancer cells having a high requirement of vitamin B6, compared to normal cells.

The VB-PdXYP of the present invention is preferable to have a molecular weight ranging from 1,000 Da to 100,000 Da (based on the weight-average molecular weight) for effective gene delivery. Further, the nucleic acid delivery complex, in which the VB-PdXYP of the present invention was conjugated to nucleic acids, is suitable to have a zeta potential ranging from 1 mV to 100 mV for effective gene Formula 4

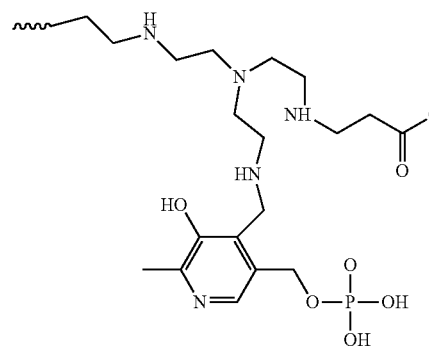 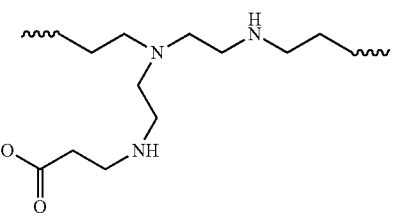

delivery, and may specifically have a zeta potential ranging from 25 mV to 50 mV. When the VB-PdXYP has physicochemical property in the range above, the VB-PdXYP of the present invention may be effectively introduced into the endosomes in cells.

Figure 16:
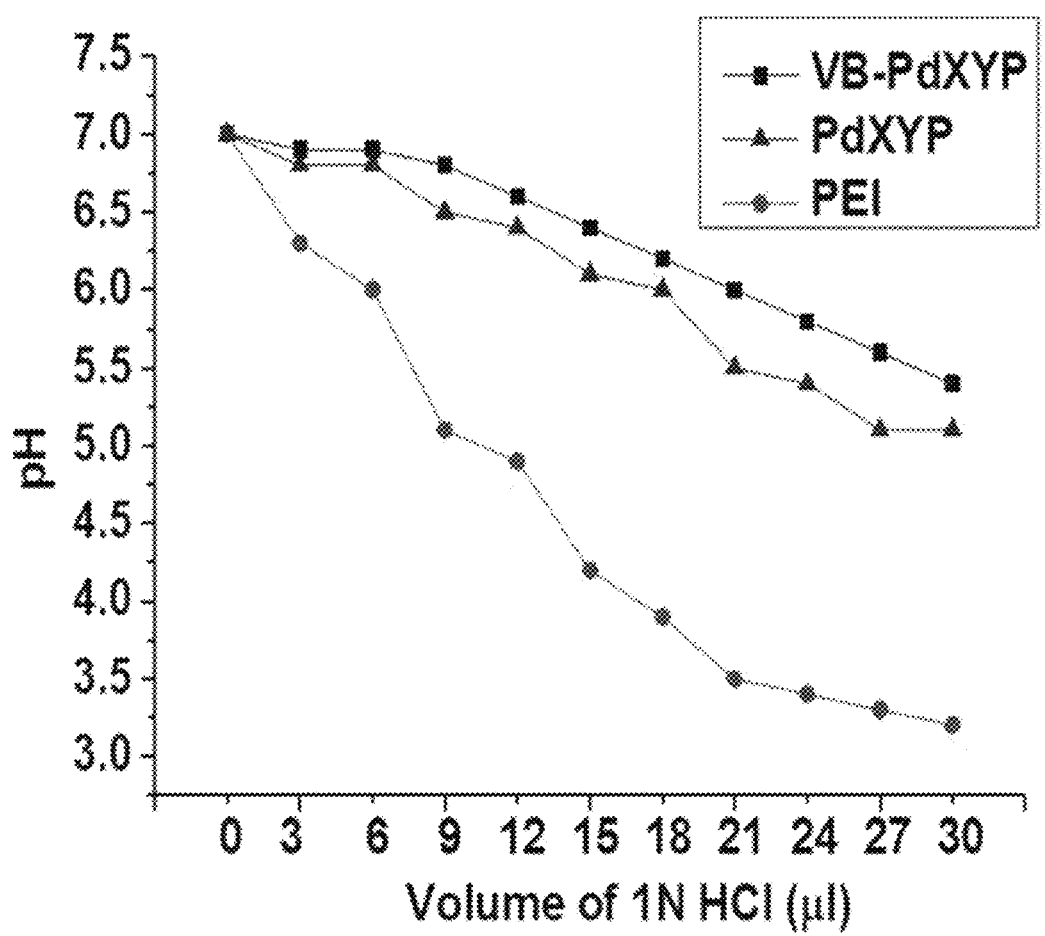
FIG. 16 shows a graph illustrating the comparison results of the buffering effects of the VB-PdXYP and the PdXYP with PEI.
Figure 17:
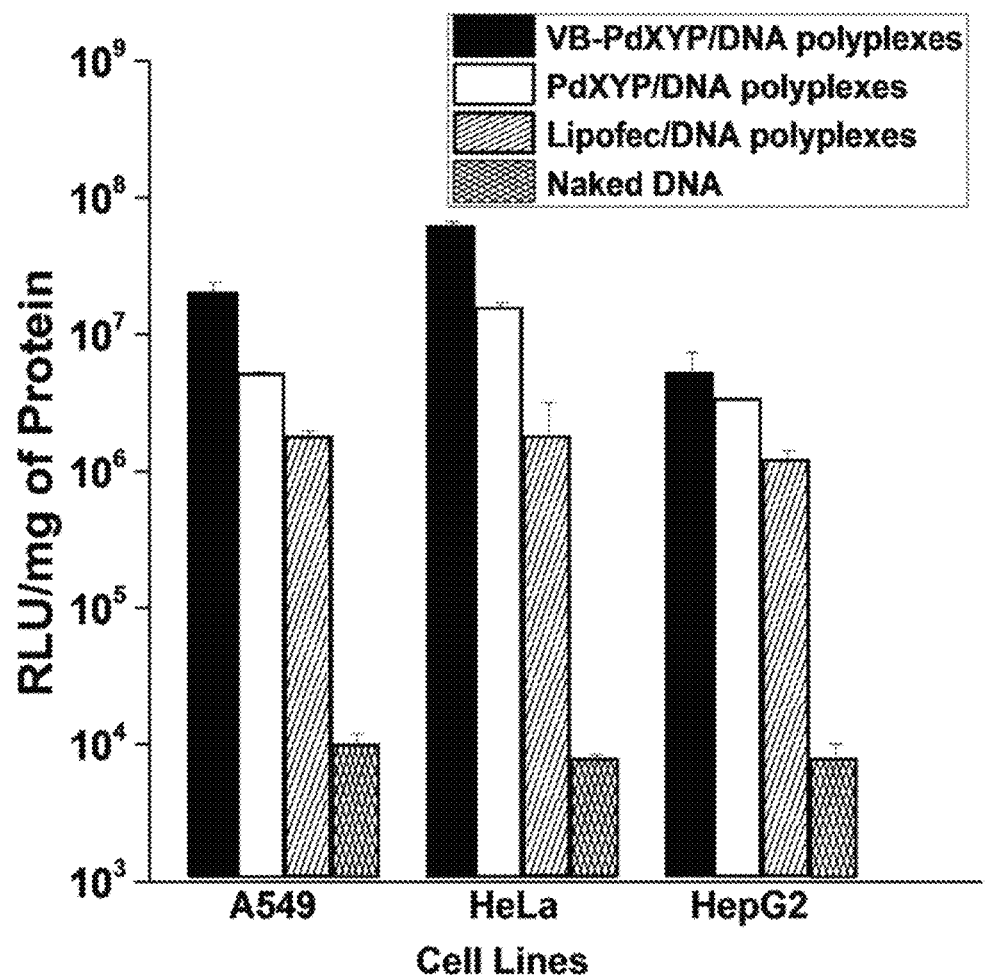
FIG. 17 shows the gene delivery efficiency of the VB-PdXYP and the PdXYP in various cell lines.

In an exemplary embodiment of the present invention, it was confirmed that the VB-PdXYP of the present invention had excellent buffering capacity and gene delivery capacity (transfection capacity) (FIGS. 16 and 17).

In another aspect, the present invention provides a method for preparing PdXYP, including preparing dixylitol diacrylate (dXYA) by esterifying dixylitol with acryloyl chloride and reacting dXYA with a low-molecular weight-PEI to obtain the PdXYP.

Specifically, the method for preparing the PdXYP may include:
a) preparing dixylitol by acetone/xylitol condensation using xylitol and acetone;
b) preparing dXYA by esterifying dixylitol prepared in step a) with acryloyl chloride; and
c) obtaining PdXYP by performing a Michael addition reaction between the dXYA prepared in step b) and low molecular weight-PEI.

In addition, the present invention provides a method for preparing the PdXYP characterized by containing vitamin B6, including preparing dXYA by esterifying dixylitol with acryloyl chloride, reacting dXYA with low molecular weight-PEI to obtain the PdXYP, and further conjugating vitamin B6 to the PdXYP.

Specifically, the method for preparing the PdXYP characterized by containing vitamin B6 of the present invention may include:
a) preparing dixylitol by acetone/xylitol condensation using xylitol and acetone;
b) preparing dXYA by esterifying dixylitol prepared in step a) with acryloyl chloride;
c) obtaining PdXYP by performing Michael addition reaction between dXYA and low molecular weight-PEI; and
d) conjugating vitamin B6 to the PdXYP prepared in step c).

In another aspect, the present invention provides a nucleic acid delivery complex, in which the PdXYP is conjugated to nucleic acids for treatment.

The types of nucleic acid for treatment that can be conjugated to the PdXYP of the present invention are not specifically limited, and any nucleic acid that can be delivered to the desired targets and show desired therapeutic effects based on the purpose of the present invention are included in the scope of the present invention. For example, the genes that can be delivered as a complex form with the PdXYP of the present invention may include normal genes of the nucleic acids for treatment associated with diseases, genes capable of inhibiting target protein expression, large and small polynucleotides including antisense polynucleotides, and genes in RNA form including ribozyme or siRNA. That is, the nucleic acid for treatment of the present invention may be selected from the group consisting of small interfering RNA (siRNA), small hairpin RNA (shRNA), endoribonuclease-prepared siRNAs (esiRNA), antisense oligonucleotides, DNA, single-stranded RNA (ss RNA), double-stranded RNA (ds RNA), DNA-RNA hybrids, and ribozymes. Particularly regarding the genes that become specific causes of diseases, the nucleic acids for treatment of the present invention may specifically be the nucleic acids that overexpress or suppress the genes, the nucleic acids corresponding to small interfering RNA (siRNA), small hairpin RNA (shRNA), endoribonuclease-prepared siRNAs (esiRNA), and antisense oligonucleotides capable of inhibiting oncogene expression, and may be the nucleic acids that can induce the expression of tumor suppressor genes. Specifically, in the present invention, the nucleic acid for treatment may be siRNA against serine hydroxymethyltransferase (SHMT), which is a vitamin B6-dependent enzyme that plays an important role in cancer cell proliferation, or esiRNA, which is a complex mixture thereof siRNA of the present invention may be esiRNA Human SHMT1 (esiRNA1, Sigma Aldrich, Cat No:EHU159081-50UG).

In addition, in the present invention, when the VB-PdXYP prepared above is used as a gene transporter, the nucleic acid for treatment may be siRNA against SHMT, which is a vitamin B6-dependent enzyme that plays an important role in cancer cell proliferation, or the complex mixture thereof, esiRNA, which may be esiRNA Human SHMT1 (esiRNA1, Sigma Aldrich, Cat No: EHU159081-50UG).

For the effective formation of the gene delivery complex of the present invention, it is suitable to react the nucleic acids for treatment with the PdXYP at molar ratios of 1:0.5 to 1:100, specifically at 1:10 to 1:40, and more specifically at 1:12 to 1:28.

Figure 3A:
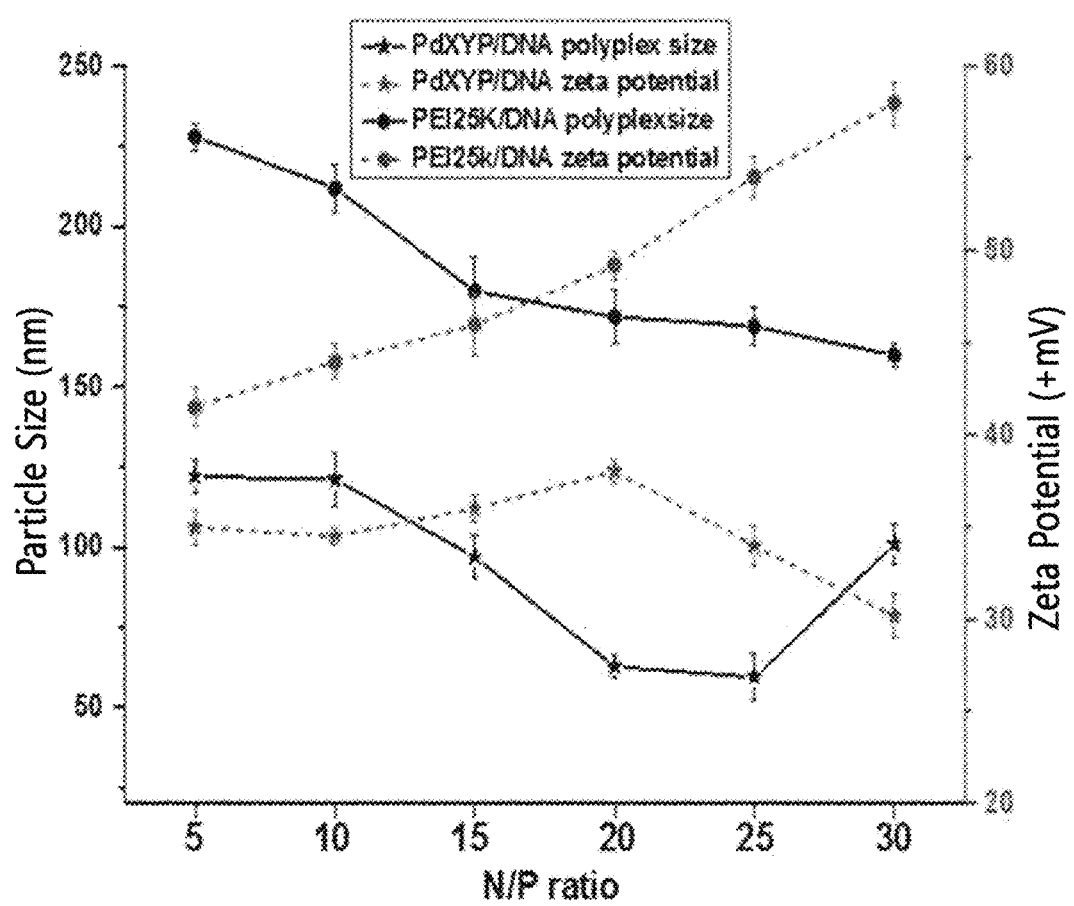
FIG. 3a shows the result from measuring particle size and zeta potential by reacting the PdXYP with DNA at various molar ratios in order to examine condensation capability and zeta potential of the PdXYP of the present invention for the nucleic acids.
Figure 3B:
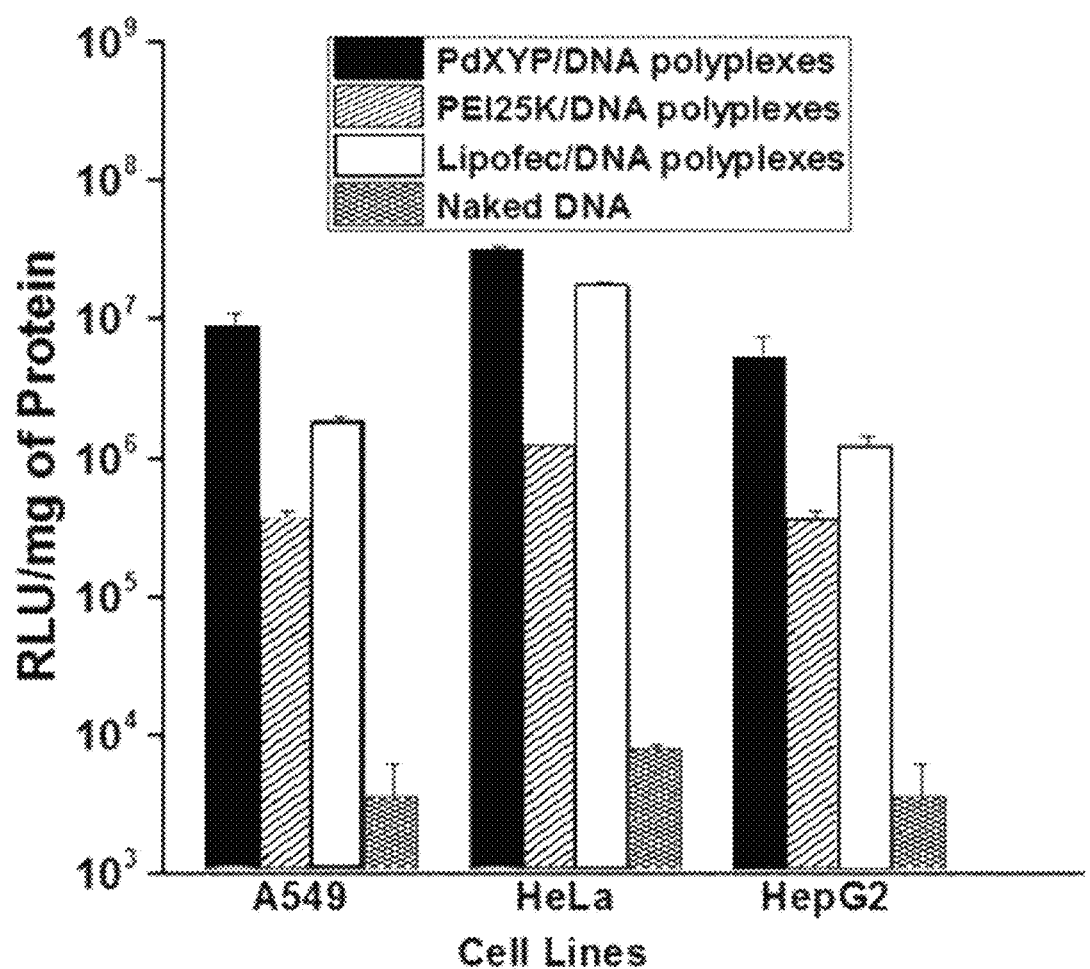
FIG. 3b shows the result from measuring luciferase expression level after treating various cells (A549 cells, HeLa cells, and HepG2 cells) with a nucleic acid delivery complex where the gene transporter is conjugated with luciferase in order to examine the transfection efficiency of the PdXYP of the present invention.
Figure 3C:
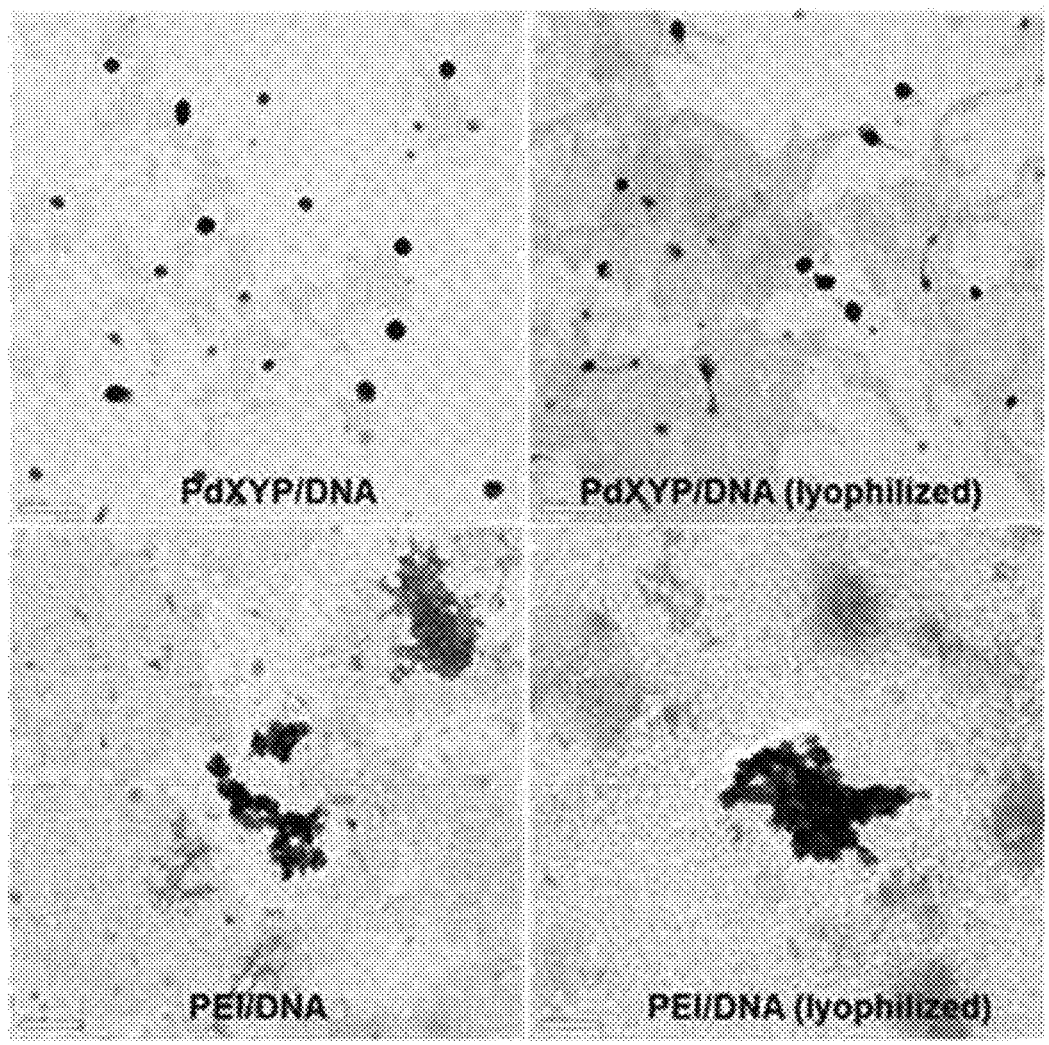
FIG. 3c shows TEM images of the nucleic acid delivery complex, where the PdXYP of the present invention is conjugated with nucleic acids, i.e., a polyplex.

The present inventors have conducted reactions between PdXYP and DNA at various molar ratios to examine the condensation capability and zeta potential of the PdXYP of the present invention for the nucleic acids for treatment. As a result, it was confirmed that the PdXYP and the gene delivery complex of DNA (PdXYA/DNA) were most effectively formed when their molar ratio was between greater than 1:10 and less than 1:30 (FIG. 3a). Because the nucleic acid delivery complex of the present invention showed relatively small and uniform distribution of average particle size ranging from 50 nm to 125 nm (FIG. 3c), it was confirmed that the nucleic acid delivery complex did not only have an appropriate particle size to be used as a gene transporter, but also showed a zeta potential where the surface charge ranged from 25 mV to 40 mV (FIG. 3a), thus capable of effectively conjugating to the anionic cell surface.

Figure 3D:
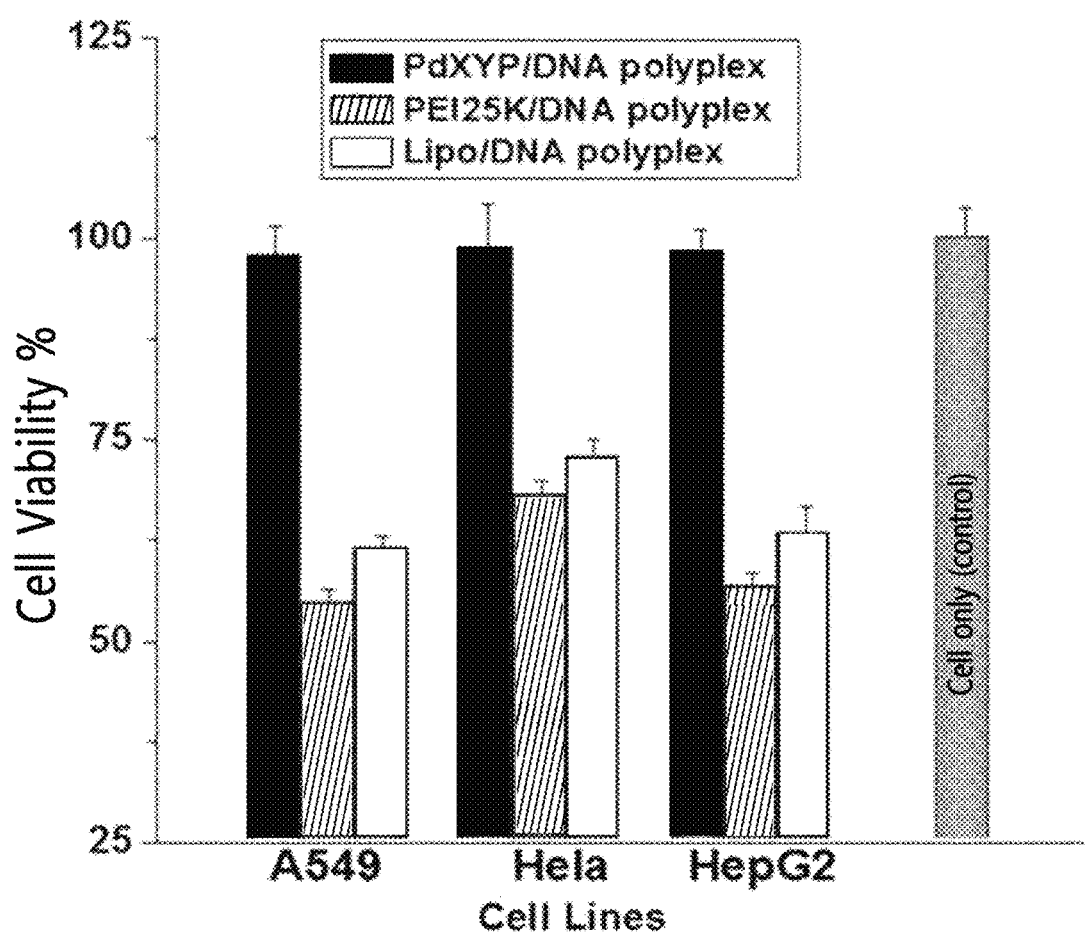
FIG. 3d shows an MTT analysis after treating various cells (A549 cells, HeLa cells, and HepG2 cells) with the nucleic acid delivery complex where the gene transporter is conjugated with luciferase in order to examine cytotoxicity of the PdXYP of the present invention.

To examine the transfection efficiency and cytotoxicity of the PdXYP of the present invention, the present inventors performed the measurement of luciferase expression and MTT analysis after treating various cells (A549 cells, HeLa cells, and HepG2 cells, FIG. 3b) with the nucleic acid delivery complex where the gene transporter is conjugated to luciferase. This was compared with the case where PEI25k and lipofectamin were used. As a result, the transfection capacity was also found to be the best compared to the control group, and specifically, cytotoxicity was hardly present, which came close to the level of the control group, in terms of cytotoxicity (FIG. 3d).

Further, in order to examine the in vivo transfection distribution and efficiency of the PdXYP of the present invention, the present inventors administered the PdXYA/pDNA nucleic acid complex to Balb/c mice (4 mice/group) by an intravenous injection and analyzed an in vivo expression and distribution. As a result, the expression was shown to increase compared to the group administered with the PEI/pDNA nucleic acid complex and specifically, a considerable increase in expression rate was observed in the brain.

The PdXYP of the present invention may be usefully used as a gene transporter for gene therapy because the PdXYP shows high binding capacity towards DNA. The PdXYP does not only form a gene delivery complex having small and uniform particle sizes that is appropriate to be used as a gene transporter, but also shows physicochemical properties that are appropriate to be used as a gene transporter by stimulating intracellular uptake route. The PdXYP also shows very low cytotoxicity in vivo and in vitro and has very high transfection efficiency, and has excellent gene delivery effect for brain tissues, which have had difficulties in gene therapy due to the BBB for a while. Further, the VB-PdXYP, in which the PdXYP of the present invention is conjugated to vitamin B6, may further enhance the gene delivery efficiency by inducing cell membrane adhesion through vitamin B6 receptors and may specifically be used for cancer treatment by having cancer tissue-specific gene delivery capacity, which has high consumption of vitamin B6.

In another aspect, the present invention provides a pharmaceutical composition for gene therapy containing the nucleic acid delivery complex, in which the PdXYP is conjugated to the nucleic acids for treatment, as an active ingredient. The pharmaceutical composition of the present invention may be used for treatment or prevention of various treatable diseases by gene therapy based on the types of the nucleic acids constituting the composition.

The pharmaceutical composition of the present invention may be administered with a pharmaceutically acceptable carrier, and for oral administration, binders, lubricants, disintegrants, excipients, solubilizers, dispersants, stabilizers, surfactants, pigments, flavoring agents, etc., other than the active ingredients may be further included. In the case of injection solutions, the pharmaceutical composition of the present invention may include buffers, preserving agents, painkillers, solubilizers, isotonic agents, stabilizers, etc. Further, the composition of the present invention may include base materials, excipients, lubricants, preserving agents, etc. for topical administration.

As described above, the formulations of the present invention may be prepared in various ways by mixing with pharmaceutically acceptable carriers, and may specifically be prepared as inhalation- or injection formulations. For example, for oral administration, the composition may be formulated into the forms of tablets, troches, capsules, elixirs, suspensions, syrups, wafers, etc., and for injections, the composition may be formulated into a unit dose administration ampoule or multiple dose administration formulation. The composition may be formulated into other solutions, suspensions, tablets, pills, capsules, sustained-release preparations, etc. The drug delivery by inhalation is one of the non-invasive methods and specifically, the delivery of nucleic acids for treatment by inhalation formulation (e.g., aerosols) may favorably be used for a wide range of treatments for lung diseases. This is because the anatomical structure and location of the lungs allow immediate and non-invasive approaches and may receive the topical application of the gene delivery system without affecting other organs.

In particular, the examples of carriers, excipients, and diluents applicable for formulations may include lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, or mineral oil. Additionally, fillers, anti-cohesive agents, lubricants, wetting agents, flavoring agents, preservatives, etc., may be further included.

The pharmaceutical composition of the present invention may be administered orally or parenterally. The administration route of the pharmaceutical composition of the present invention is not limited thereto, but for example, oral, intravenous, intramuscular, intra-arterial, intramedullary, intradural, intracardiac, dermal, subcutaneous, intraperitoneal, intestinal, hypoglossal, or topical administrations are possible. For such clinical administrations, the pharmaceutical composition of the present invention may be formulated into proper formulations using a known technique. For example, for oral administration, the pharmaceutical composition may be mixed with inert diluents or edible carriers and sealed in hard or soft gelatin capsules or compressed into tablets and administered. In the case of oral administration, active ingredients may be mixed with excipients and used as forms of tablets for ingestion, buccal tablets, troche, capsules, elixirs, suspensions, syrups, wafers, etc. Further, various formulations including injections, parenteral administrations, etc., may be prepared by known methods or conventional methods in the technical field.

The effective administration dose of the pharmaceutical composition of the present invention has a wide range depending on the weight, age, sex, health conditions, diet of the patient, administration time, administration method, excretion rate, and the severity of diseases, and may be readily determined by one of ordinary skill in the art.

With respect to the pharmaceutical composition of the present invention, the nucleic acids for treatment constituting the composition, may target an inhibition of serine hydroxymethyltransferase (SHMT) expression and specifically, the nucleic acids for treatment may be esiRNA Human SHMT1 (esiRNA1, Cat No: EHU159081-5OUG). The pharmaceutical composition of the present invention may have effects for treating or preventing cancer based on the types of the nucleic acids for treatment constituting the pharmaceutical composition, and the cancer may be selected from the group consisting of lung cancer, bone cancer, pancreatic cancer, skin cancer, head and neck cancer, skin melanoma, uterine cancer, ovarian cancer, rectal cancer, colorectal cancer, colon cancer, breast cancer, uterine sarcoma, fallopian tube carcinoma, endometrium carcinoma, cervix carcinoma, vagina carcinoma, vulva carcinoma, esophageal cancer, small intestine cancer, thyroid cancer, parathyroid cancer, soft tissue sarcoma, urethral cancer, penile cancer, prostate cancer, chronic or acute leukemia, pediatric solid tumor, differentiated lymphoma, bladder cancer, kidney cancer, renal cell carcinoma, renal pelvic carcinoma, primary central nervous system lymphoma, myelencephalon tumor, brain stem glioma, and pituitary gland adenoma.

In another aspect, the present invention provides a method for gene therapy using the PdXYP of the present invention explained above and the nucleic acid delivery complex including the PdXYP or the pharmaceutical composition containing the PdXYP.

Mode for Carrying Out the Invention

Hereinafter, the present invention will be described in details with reference to the following Examples. However, these Examples are for illustrative purposes only, and the scope of the present invention is not limited thereto.

Example 1: Used Samples and Material

In the present invention, the polydixylitol diacryloylate polymer gene transfer, PdXYP, of the present invention was prepared and the sample and materials shown below were used to confirm the Examples.

Branched Poly (ester imine), Mn: 1.2 k and 25 k (bPEI), dimethyl sulfoxide (DMSO), bafilomycin A1, and MTT (3-(4,5-dimethyl thioazol-2-yl)-2,5-diphenyl tetra-zolium bromide) reagents used were purchased from Sigma products (St. Louis, Mo., USA). Further, luciferase reporter that code for firefly (*Photonus pyralis*), pGL3-vector and enhancer were obtained from Promega (Madison, Wis., USA). Green fluorescent protein (GFP) genes were obtained from Clontech (Palo Alto, Calif., USA). Tetramethylrhodamine isothiocyanate (TRITC) and YOYO-1 iodide (Molecular Probes, Invitrogen, Oreg., USA) dyes were used for a confocal microscope analysis.

Example 2: Preparation of PdXYP

The PdXYP of the present invention was synthesized in three steps as shown below (FIG. 1).

2-1. Dixylitol Synthesis

The present inventors have noticed that the number and stereochemistry of the hydroxyl groups affect the intracellular delivery, and thus, have tried to develop material for gene delivery that has enhanced delivery efficiency in the cells by controlling osmotically active hydroxyl group. Since sugar alcohols having 8 hydroxyl groups are not commercially available, the present inventors have directly synthesized dixylitol, the xylitol dimer, as an analogue of an octamer by the procedure presented in FIG. 1.

Specifically, xylitol was first crystallized into diacetone xylitol (Xy-Ac) crystalline by the acetone/xylitol condensation method of Raymond and Hudson. The terminal hydroxyl group of Xy-Ac was reacted with trifluoromethyl sulphonyl chloride ($CF_3SO_2$—O—$SO_2CF_3$) to produce trifluoromethane sulphonyl xylitol (TMSDX). The prepared TMSDX was reacted with the same molar amount of Xy-Ac in the presence of dry THF to form dixylitol diacetone (Xy-Ac dimer). The reaction product was finally converted into the xylitol dimer by opening the chemical rings in the HCl/MeOH solution ((a) of FIG. 1).

2-2. Synthesis of dXYA

Dixylitol diacrylate (dXYA) monomer was synthesized by an esterification of dixylitol with 2 equivalents of acryloyl chloride. An emulsion was prepared by dissolving dixylitol (1 g) in DMF (20 mL) and pyridine (10 mL), followed by a dropwise addition of acryloyl chloride solution (1.2 mL dissolved in 5 mL DMF) at 4° C. with constant stirring. After completing the reaction, HCl-pyridine salts were filtered and the filtrate was added dropwise to diethyl ether. The product was precipitated with syrup liquid and dried under vacuum.

2-3. Synthesis of PdXYP

The PdXYP of the present invention was prepared by a Michael addition reaction between low-molecular weight bPEI (1.2 k) and dXYA.

Specifically, the synthesized dXYA (0.38 g) dissolved in DMSO (5 mL) was added dropwise to 1 equivalent of bPEI (1.2 kDa, dissolved in 10 mL DMSO) and reacted at 60° C. with constant stirring for 24 hours. After completing the reaction, the mixture was dialyzed using a Spectra/Por membrane (MWCO: 3500 Da; Spectrum Medical Industries, Inc., Los Angeles, Calif., USA) for 36 h at 4° C. against distilled water. Finally, the synthesized polymer was lyophilized and stored at −70° C.

Figure 4:
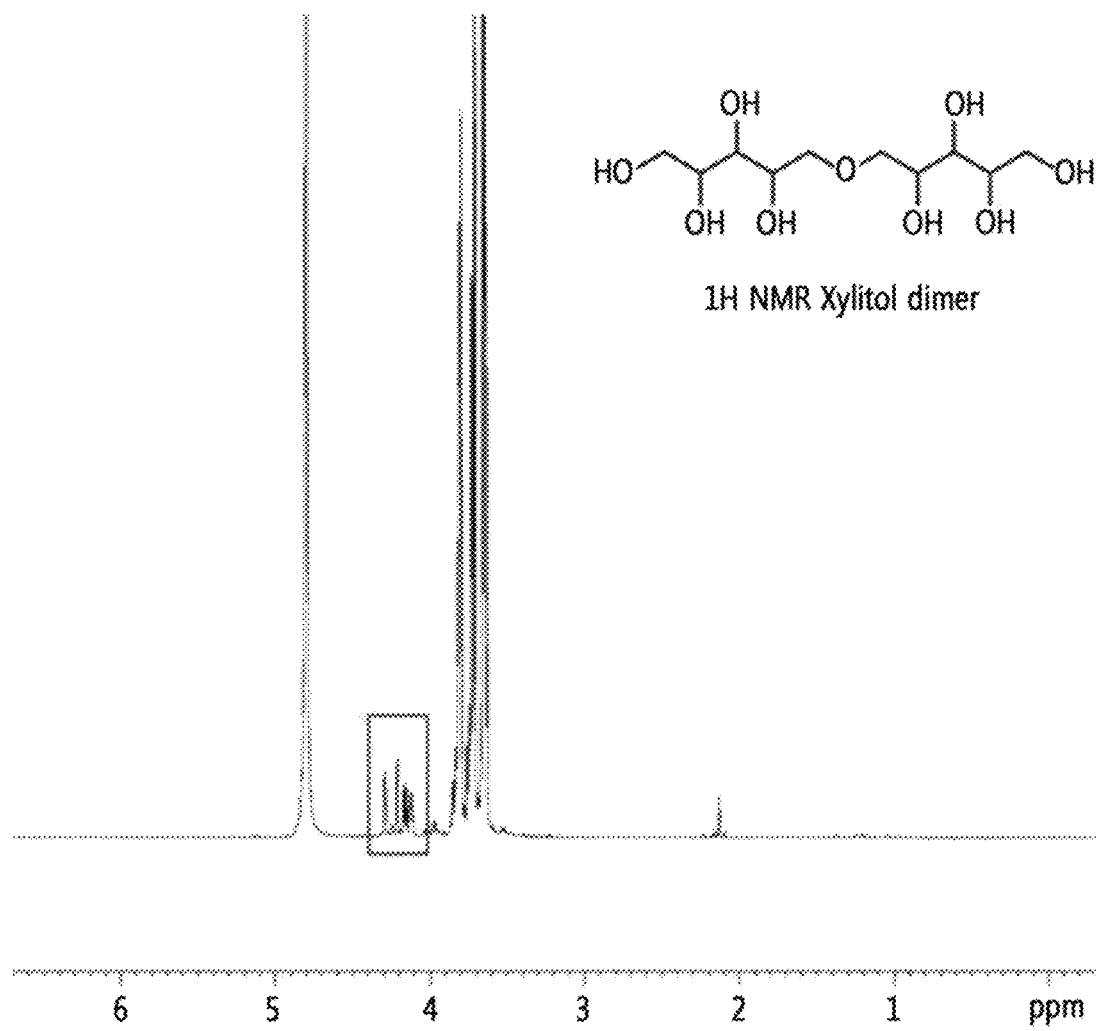
FIG. 4 shows that a xylitol dimer, which is dixylitol, has been produced by $^1$H NMR.
Figure 5:
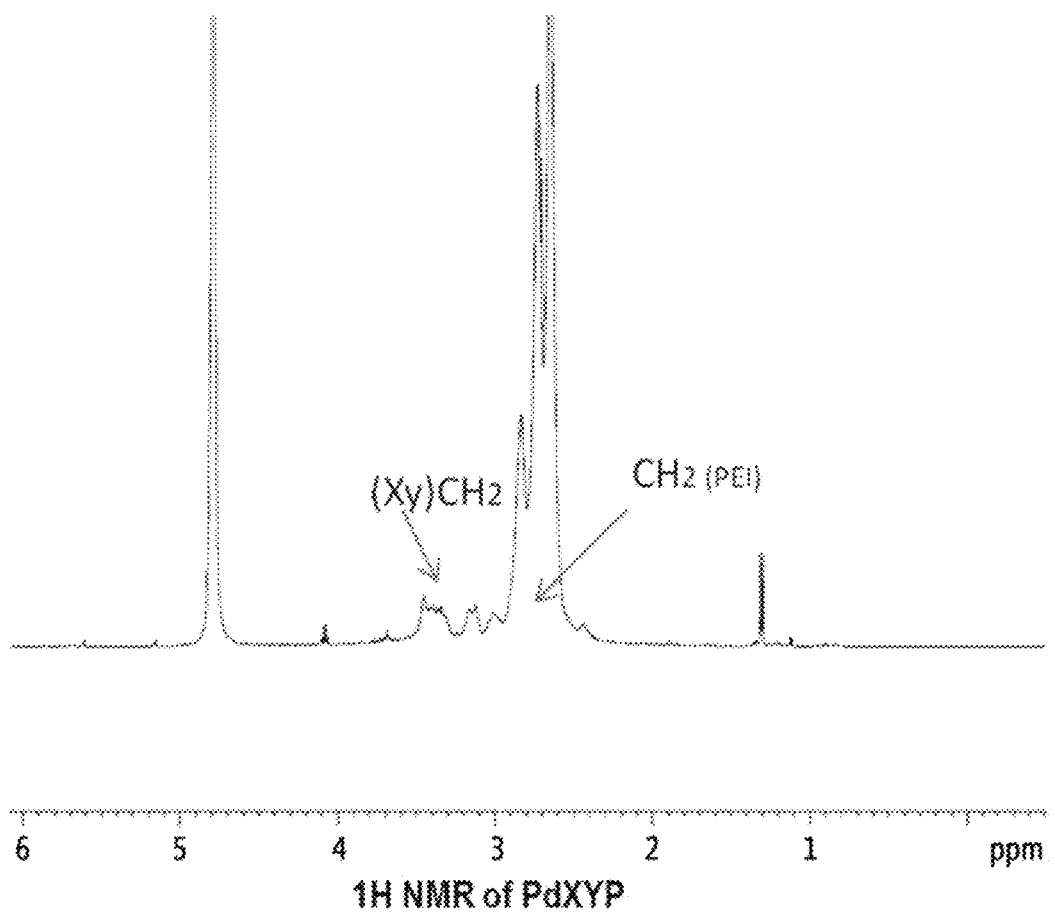
FIG. 5 shows that the PdXYP of the present invention has been produced by $^1$H NMR.

As indicated in FIGS. 4 and 5, PdXYP was confirmed to be successfully synthesized.

2-4. PdXYP Nanoplex Formation

Figure 6:
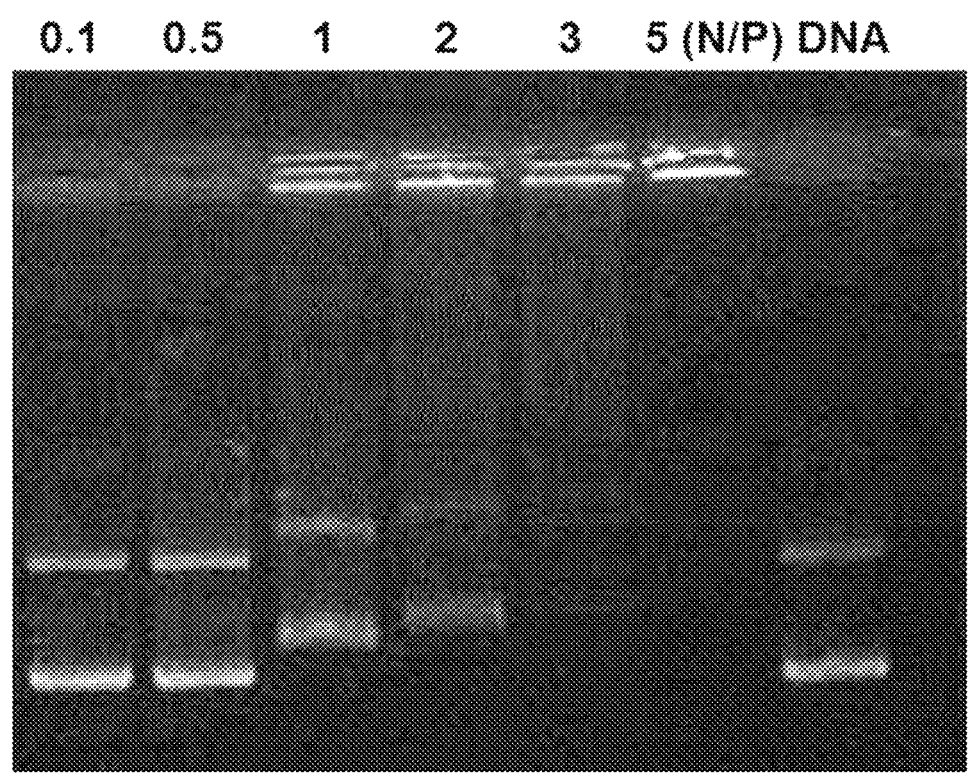
FIG. 6 shows the result of gel retardation on forming property, which produces polyplex by conjugating the PdXYP with pDNA, and also shows the result of gel electrophoresis on PdXYP/DNA polyplex formed by reacting the PdXYP with DNA at molar ratios (N/P) of 0.1, 0.5, 1, 2, 3, and 5.

The forming property, in which the PdXYP of the present invention forms polyplexes by binding to pDNA, was confirmed by gel retardation and DNase protection assay. Specifically, the PdXYP/DNA polyplex, which was generated by reacting PdXYP with DNA at molar ratios (N/P) of 0.1, 0.5, 1, 2, 3, and 5, was subjected to gel electrophoresis to conduct the gel retardation. As a result, as indicated in FIG. 6, the polyplex was effectively formed at molar ratios (N/P) of 0.1, 0.5, 1, and 2.

Figure 7:
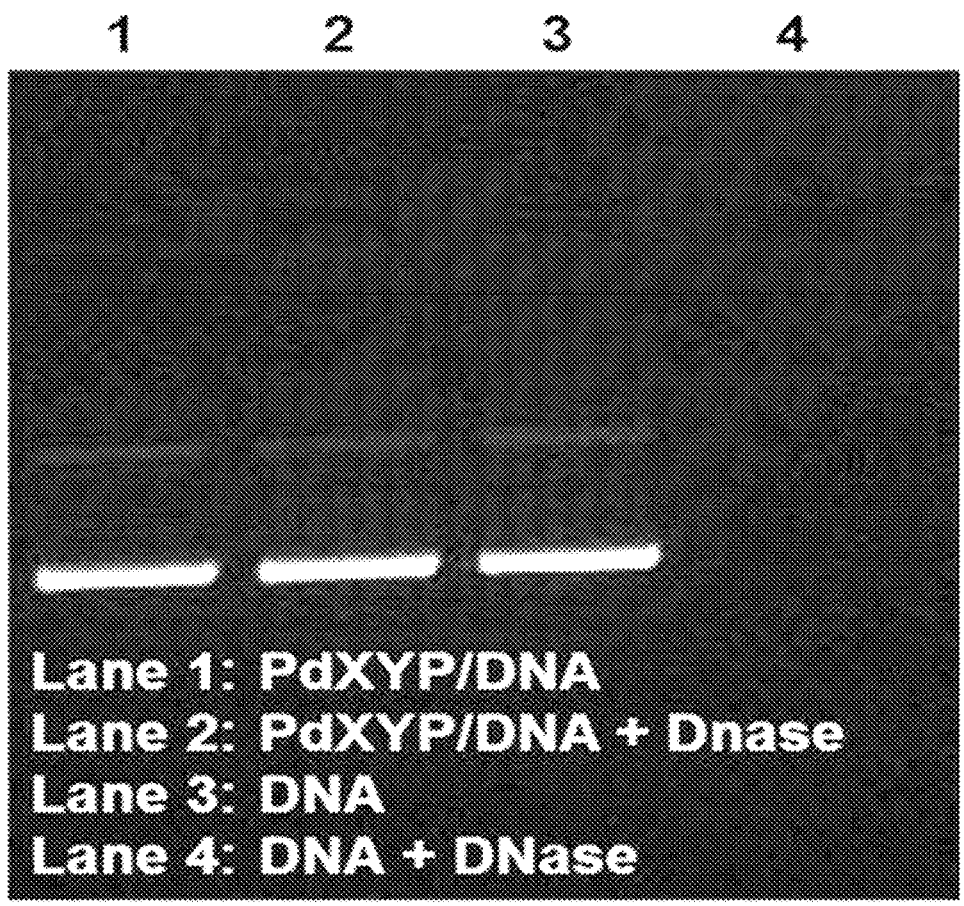
FIG. 7 shows the result of DNase protection assay on forming ability, which forms a polyplex by conjugating the PdXYP with pDNA. The capacity to protect DNA was confirmed with the PdXYP/DNA polyplex, the group of the PdXYP/DNA polyplex treated with DNase, DNA, and the group of DNA treated with DNase by gel electrophoresis.

Further, the capacity to form the polyplexes by conjugating PdXYP with pDNA, which would protect DNA from DNase was confirmed by DNase protection assay. Particularly, the capacity to protect DNA was confirmed by the PdXYP/DNA polyplex, the group in which PdXYP/DNA polyplex was treated with DNase, DNA, and the group in which DNA was treated with DNase through gel electrophoresis. As a result, as indicated in FIG. 7, it was confirmed that DNA was almost perfectly protected from DNase when PdXYP/DNA polyplex was formed.

Example 3: Experiment on Gene Delivery Efficiency of PdXYP 3-1. Cell Culture and Animal Studies In order to confirm the gene delivery efficiency using the PdXYP of the present invention prepared in Example 2, experiments were conducted in vitro and in vivo.

Particularly, with respect to the cell culture, human hepatocellular liver carcinoma cells (HepG2) and human uterine cervix epithelial carcinoma cells (HeLa) were cultured in low glucose DMEM (Sigma, USA) containing 10% fetal bovine serum. Adenocarcinoma human alveolar basal epithelial cells (A549) were cultured in Roswell Park Memorial Institute (RPMI)-1640 culture medium containing 1% antibiotic cocktail of penicillin/streptomycin and 10% heat-inactivated FBS (Hyclone Laboratories, USA). Further, all the cells were maintained under standard culture conditions of 37° C. and 5% $CO_2$.

In particular, with respect to the animal studies, C57BL/6 mice were obtained from the Human Cancer Consortium National Cancer Institute (Frederick, Md., USA) and kept in a laboratory animal facility maintained at a temperature of 23° C.±2° C., a humidity of 50%±20%, under a 12 h light-dark cycle. All the experimental protocols for this experiment were reviewed and approved by the Animal Care and Use Committee at Seoul National University (SNU-120409-3).

3-2. In Vitro BBB Transmigration Assay

Since the ultimate purpose for the preparation of the gene transporter lies in an in vivo application, an in vitro BBB model was established to test the capacity of the PdXYP/DNA polyplex of the present invention.

Figure 8A:
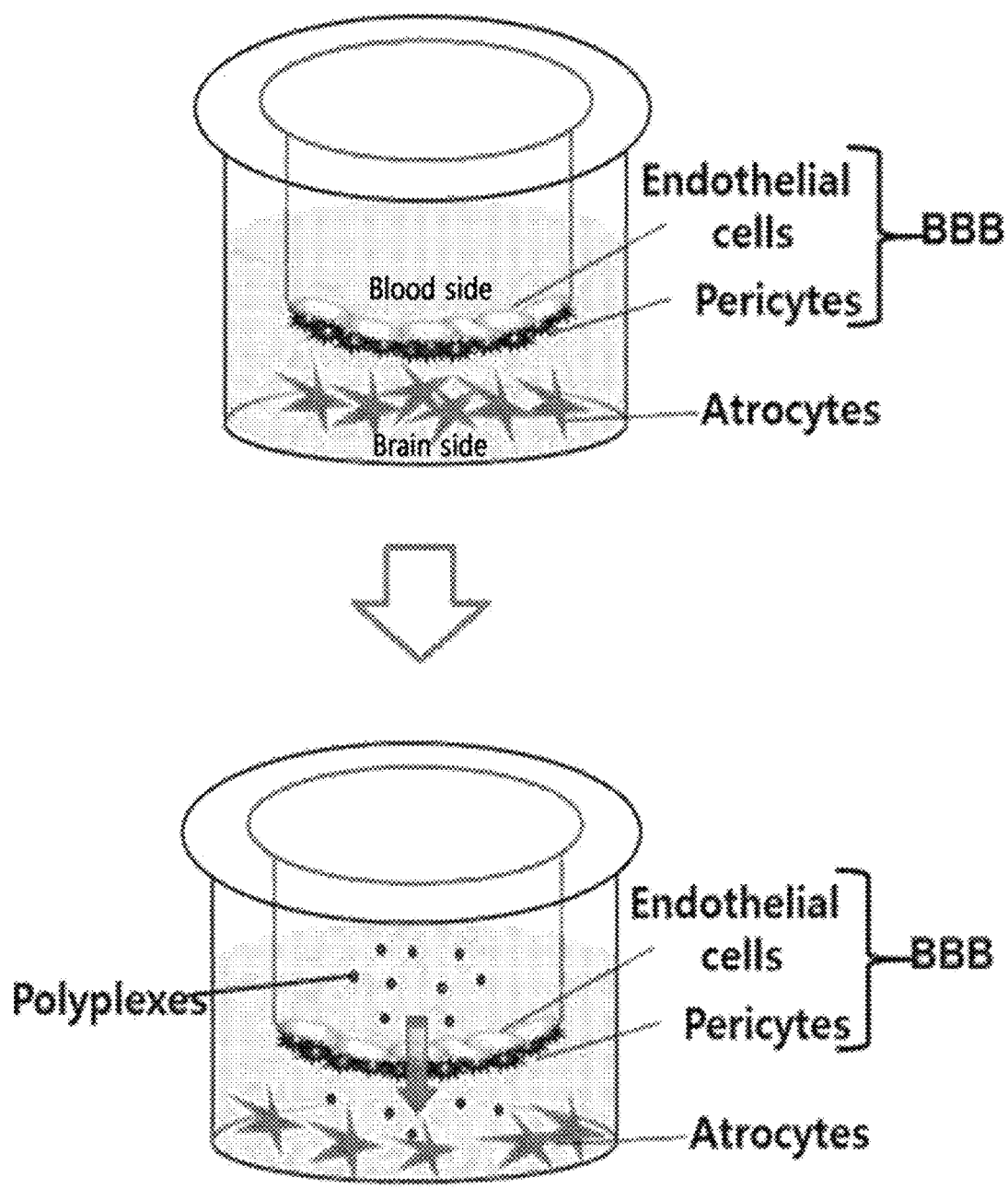
FIG. 8a shows a schematic diagram illustrating the gist of the in vitro BBB transmigrating experiment on the PdXYP/DNA polyplex of the present invention.

All the BBB transmigration experiments were conducted on day 6 of the BBB culture. The cultured upper chamber of the BBB was treated with fluorescence (FAM)-labeled pDNA (pGL3), PdXYP-pGL3 nanoplex, and PEI-pGL3. For all the upper and lower chambers, the media were fixed as 1 mL. After an addition of the pDNA (pGL3), PdXYP-pGL3 and PEI-pGL3 nanoplexes and incubation at 37° C. for 2 h, the media were aspirated from the upper and the lower chambers, respectively, and analyzed spectrofluorometrically (FIG. 8*a*).

Figures 8B, 8C:
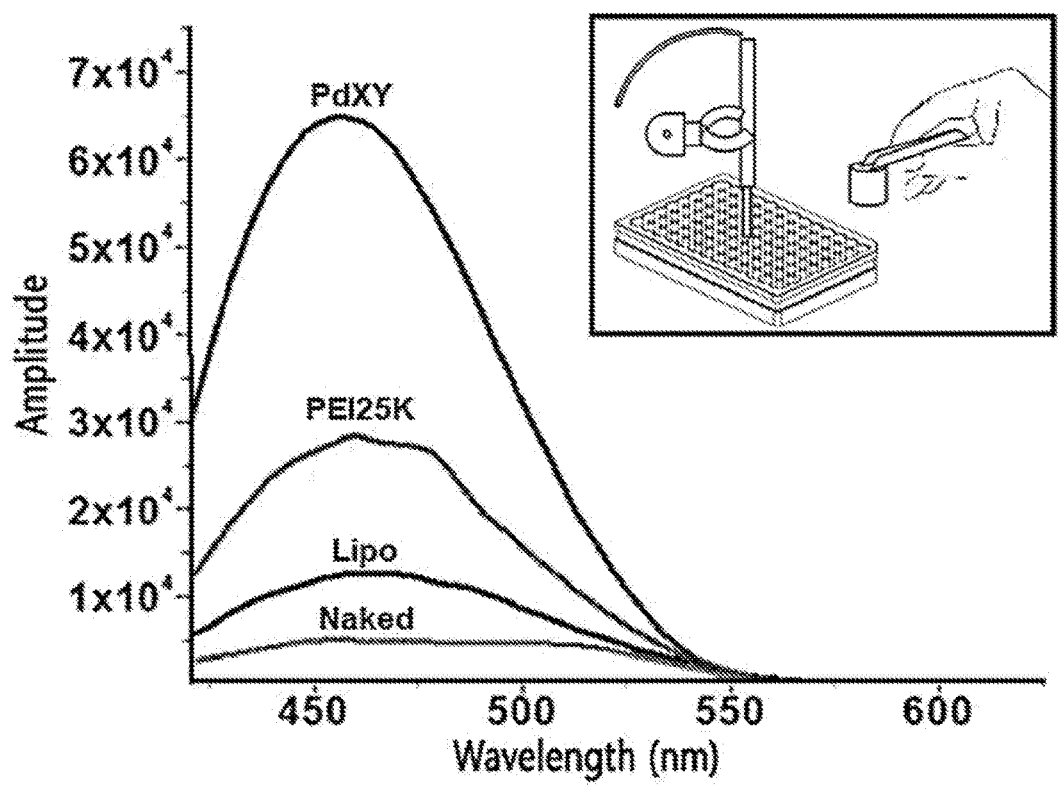
FIG. 8b shows the in vitro BBB transmigration rate of the PdXYP/DNA polyplex of the present invention. Specifically.
FIG. 8c shows the measurement result of the values of the transendothelial electrical resistance (TEER), before and after treating an in vitro BBB with the PdXYP/DNA polyplex of the present invention.

As a result, after 4 hours of PdXYP/DNA polyplex treatment in the upper chamber (blood side), 40% of the original fluorescence amount was found in the lower chamber (brain side). When the same model was treated with free pDNA, only 1% of the original fluorescence was found in the lower chamber (FIG. 8*b*). These results show that the transmigration efficiency of pDNA across the BBB considerably increases following complexation of the PdXYP with pDNA.

Further, the result on measuring the transendothelial electrical resistance (TEER) values of the BBB was confirmed, before (214±2.52 ohm/cm$^2$) and after (211.33±2.80 ohm/cm$^2$) the PdXYP/DNA polyplex treatment. Because TEER values have the inevitable relationship with the functions of the BBB, the results show that the PdXYP/DNA nanoplexes do not cause any functional damages to the BBB while traversing through the barrier (FIG. 8c).

In subsequent experiments, the present inventors measured the efficiency where the PdXYP/pDNA polyplexes are delivered to astrocyte cells in the lower chamber of the BBB model. This was measured by treating the upper chamber with the PdXYP/pDNA polyplex expressing luciferase. After 48 hours, the brain cells in the bottom of the chamber showed a significant level of luciferase expression after measuring luminescence. The results show that the PdXYP/DNA polyplex retains its function, that is, the gene delivery function, even after transmigrating the BBB.

3-3. In Vivo Luciferase Expression Bioimaging and Biodistribution

In the in vivo bioimaging experiment, in vivo gene delivery capacity, that is, transfection efficiency was confirmed by intravenously injecting 6 week old mice with the PdXYP/pDNA complex and confirming the luciferase expression in each organ.

Specifically, 6 week old nude Balb/c mice (male, 4 mice/group) were intravenously injected with 100 μL of Polyplex (PdXYP, PEI, and naked pGL3) suspension. The IVIS imaging system 100 (Xenogen) with Living Image software was used for tumor bioimaging to analyze the luciferase expression in different organs of mice. 3 days after the tail intravenous injection, the mice were anesthetized by an intraperitoneal (IP) injection of zoletil (40 mg/kg):rompun (10 mg/kg) (4:1) mixture diluted 8 times in sterilized 1×PBS. 200 μL of D-luciferin (15 mg/mL stock in DPBS) for 20 g mouse (3 mg/mouse) was injected intraperitoneally, which quickly distributed throughout the body. Luciferase-expressed cells containing enzyme were reacted with luciferin to emit luminescence, and the luminescence level was measured by the IVIS system and the luciferase expression level was measured.

The luminescence level was measured in plateau phase, which usually occurs 15 minutes after the reaction with luciferin and lasts for 15 minutes to 20 minutes. The level of luciferase protein expression was quantified using the lysates in which each organ of mice was extracted and homogenized by luminometer.

Figure 9A:
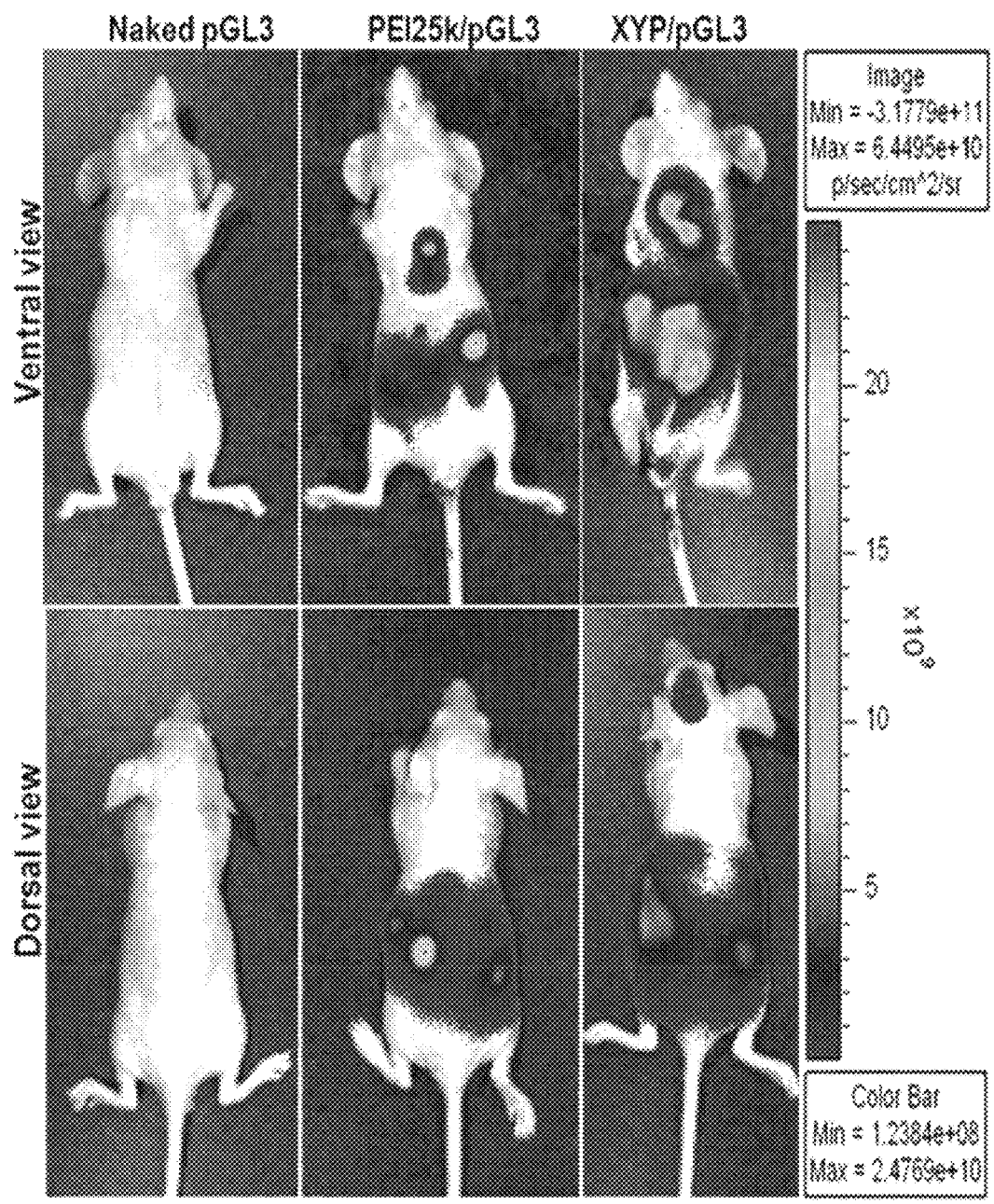
FIG. 9a shows the result from bioimaging of in vivo luciferase expression to confirm in vivo gene delivery capacity, i.e., transfection efficiency, of the PdXYP/DNA polyplex of the present invention. Specifically.
Figure 9B:
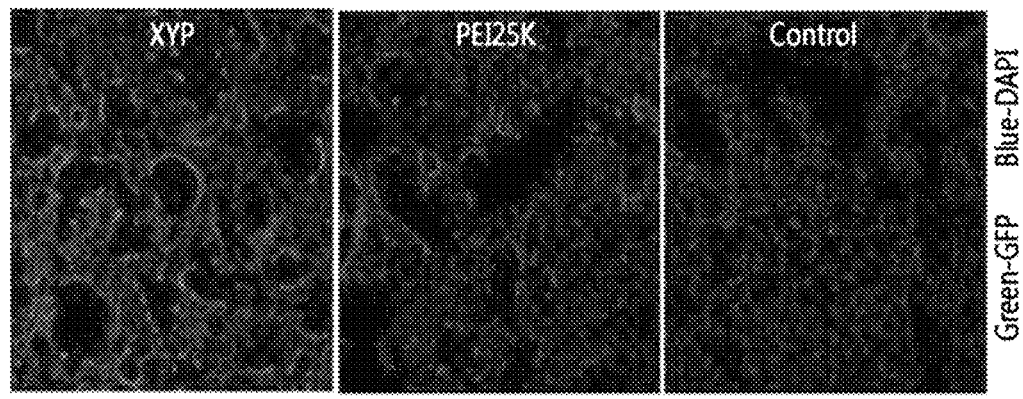
FIG. 9b shows a luciferase expression rate, i.e., in vivo transfection, in brain tissues of mice models, after administering the PdXYP/pDNA polyplex, the PEI/pDNA polyplex, and the naked pGL3 DNA to mice.
Figure 9C:
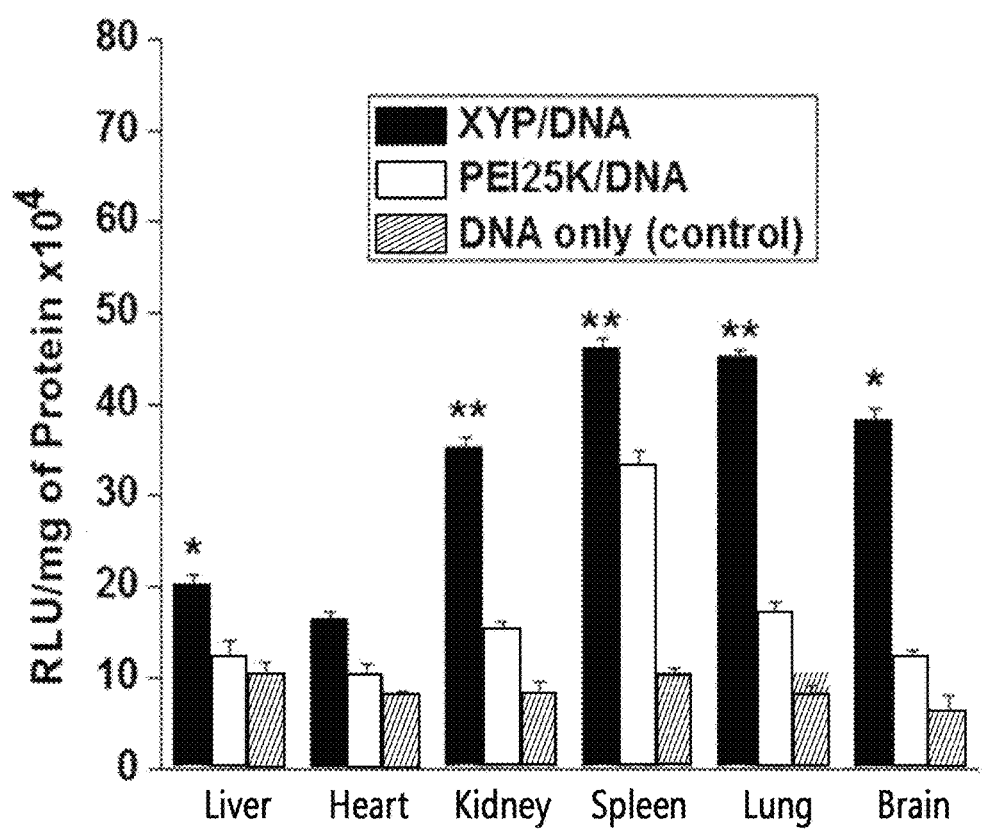
FIG. 9c shows a graph illustrating in vivo transfection efficiency measured in each of the tissues such as liver, heart, kidney, spleen, lung, and brain tissues of the mice models by comparing luciferase expression rate after administering the PdXYP/pDNA polyplex, the PEI/pDNA polyplex, and the naked pGL3 DNA to mice.

As the result of bioimaging, the group administered with the PdXYP/pDNA had increased expression compared to the group administered with the PEI/pDNA polyplex, and specifically showed considerably increasing expression rate in the brain (FIGS. 9a to 9c).

The results confirmed that the in vivo gene delivery efficiency is more remarkable compared to the existing gene transporters when the PdXYP of the present invention is used as a gene transporter and that the genes are effectively delivered to the brain tissues, which had very low delivery efficiency upon the use of the existing gene transporters.

Example 4: In Vitro Transfection and Cytotoxicity Studies 4-1. Cytotoxicity Experiment of the PdXYA/DNA Complex In vitro cytotoxicity of the PdXYP was evaluated by MTT analysis in three types of cell lines (A549, HeLa, and HepG2) and compared with lipofectamine and PEI 25 kDa. At monolayer confluence, the cells were trypsinized, seeded in a 24-well plate at an initial cell concentration of 10×10$^4$ in 1 mL growth medium, and cultured at 80% confluence prior to the polyplex treatment. The cells were treated in serum-free medium, which was replaced with a serum-containing medium 3 hours later. After 36 hours, 500 μL of MTT solution (0.5 mg/mL in 1×PBS) was added to each well and treated for 3 hours. The medium was removed and the generated purple formazan crystals were dissolved in 500 μL of DMSO. The dissolved formazan (100 μL) from each well was transferred to a 96-well plate and absorbance was measured at a wavelength of 540 nm using a VERSAmax tunable microplate reader (Sunnyvale, Calif., USA). Every experiment was repeated three times.

Figure 10:
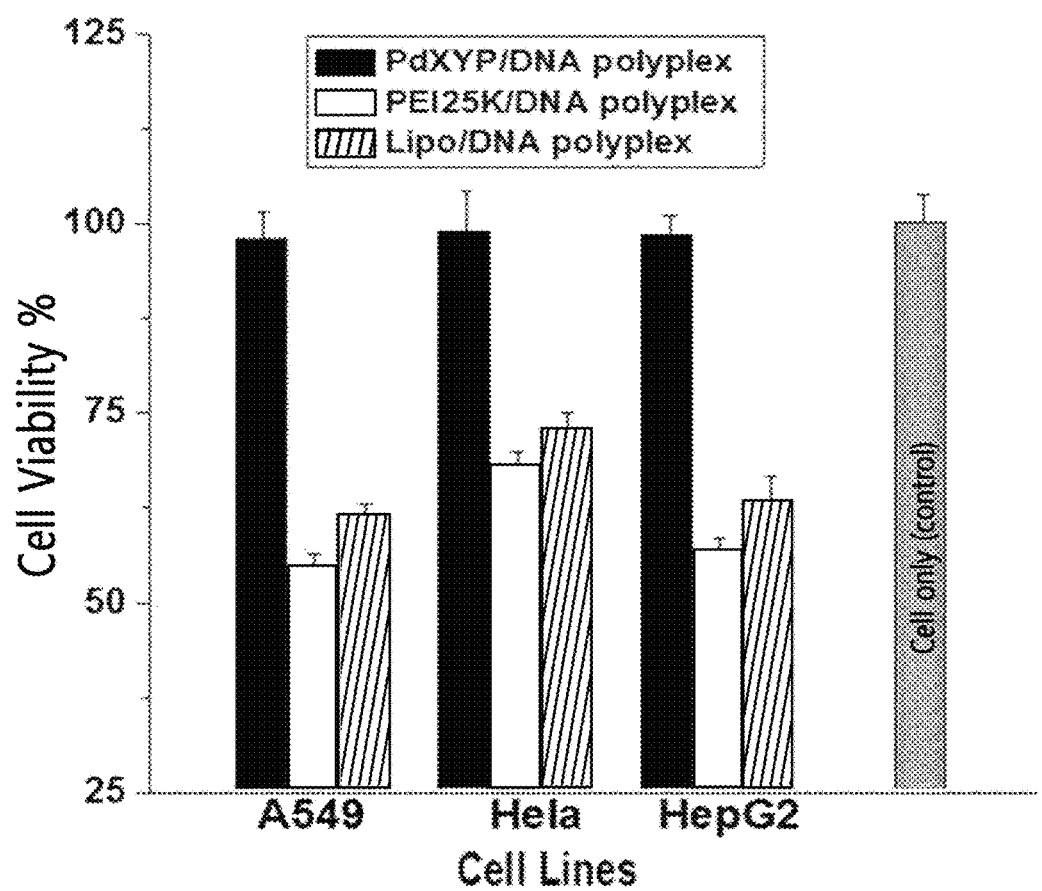
FIG. 10 shows the results of evaluation of in vitro PdXYP cytotoxicity in three different types of cell lines (A549, HeLa, and HepG2) by MTT analysis and comparison of the cytotoxicity with PEI 25 kDa and lipofectamine.

As a result, as indicated in FIG. 10, it was confirmed that cell viability was quite high as 95% at a high concentration, which was a quite high value compared to the high toxicity of lipofectamine and PEI 25 kDa that have been widely used in commercial markets. These results suggest that the PdXYP has low cytotoxicity by having a biodegradable ester bond between the dXY and a low-molecular weight PEI and biocompatibility of polyxylitol. In particular, low cytotoxicity may be due to low charge density compared to PEI 25 kDa (FIG. 10).

4-2. In Vitro Transfection of PdXYA/DNA Complex

Figure 11:
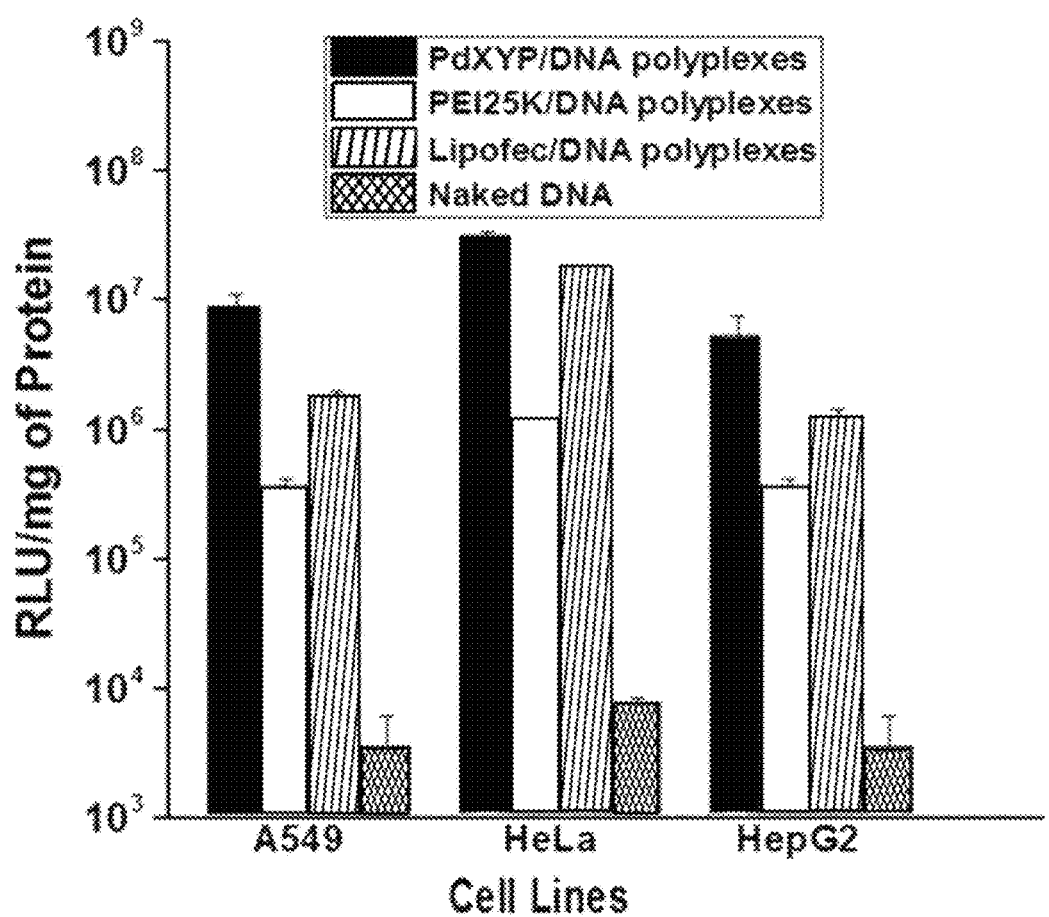
FIG. 11 shows the measurement result of transfection efficiency after treating three different types of cell lines (A549, HeLa, and HepG2) with the PdXYP/DNA, the PEI/DNA, and the lipofectamine/pDNA.

Transfection efficiency was measured by treating the three types of cell lines (A549, HeLa, and HepG2) with PdXYP/DNA, PEI/DNA, and lipofectamine/pDNA. As a result, as indicated in FIG. 11, the transfection efficiency was improved when using the PdXYP as a gene transporter compared to the positive control. As the N/P ratio became high, the PdXYP showed higher transfection efficiency and cell line-dependent transfection efficiency, and specifically, showed the highest transfection efficiency in the HeLa cell line. The transfection efficiency in malignant tumor cells was higher than in normal cells, and in some cases, it was about 40 times higher. For example, the ratio of transfected GFP-positive HeLa cells under the N/P 20 condition reached 40%, whereas the ratio of transfected cells of normal cells was generally less than 1%. Further, the GFP expression level in the HeLa cells was about 10,000 times higher.

Example 5: Co-Localization Measurement and Caveolin Expression

The present inventors have tried to confirm by which mechanisms the remarkable in vitro and in vivo transfection capacity of PdXYP/DNA polyplex that were confirmed in the Examples follow.

Figure 12:
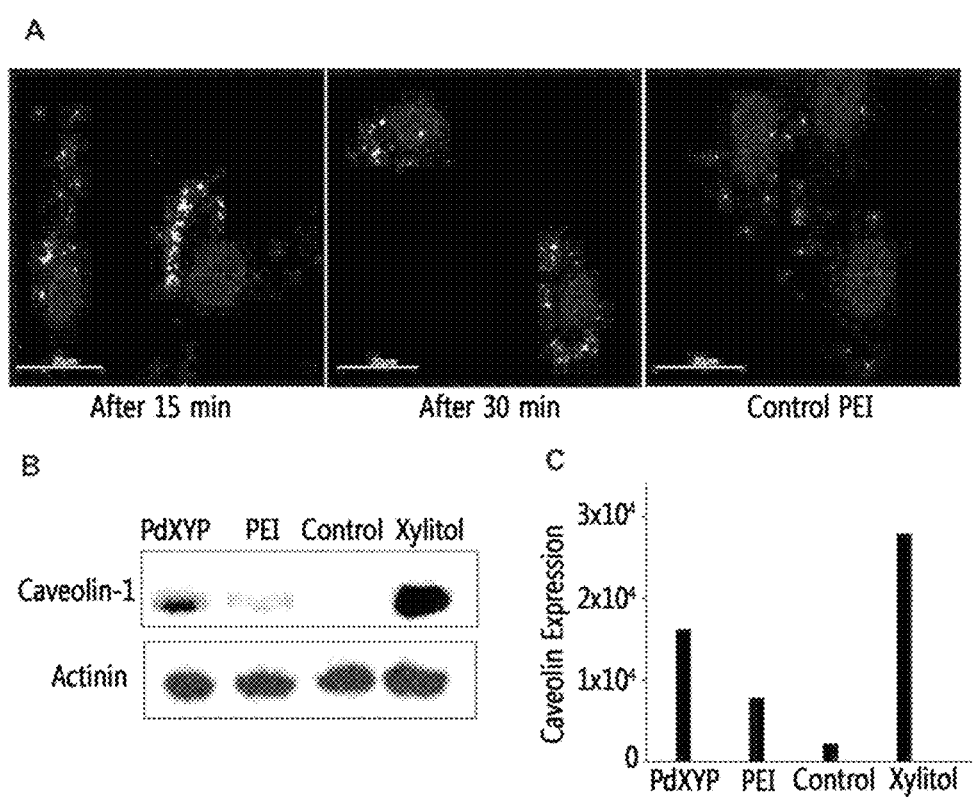
FIG. 12A-C shows the co-localization of lipid raft and the PdXYP/DNA polyplex and inducing capacity of caveolin expression using a lipid raft labeling kit (Invitrogen).

The co-localization of lipid raft and the polyplex was confirmed based on staining protocol provided by manufactures, using the lipid raft labeling kit (Invitrogen) (FIG. 12).

As a result, it was confirmed that the PdXYP/DNA polyplexinduced caveolae-mediated endocytosis, and colocalized with the lipid raft (A of FIG. 12). This shows that hyperosmotic extracellular disturbance caused by the polyol group of polyxylitol dimers induces the increase in caveolin-1 expression (B and C of FIG. 12), followed by increasing caveolae-mediated endocytosis.

Example 6: Comparison of Physicochemical Property, Osmotic Activity, and Transfection Capacity Between the PMGT and the PdXYP The present inventors have confirmed superiority in the gene transporter of the present invention by comparing previously produced polymannitol based gene transporter (PMGT) and the PdXYP of the present invention.

6-1. Preparation of PMGT

To confirm superiority in the PdXYP of the present invention, the PMGT with similar structure was prepared. This was the gene transporter prepared by the present inventors, which was disclosed Korean Patent Application Publication No. 10-2014-0043962, and the gene transporter was prepared by the methods disclosed in the corresponding patent (FIG. 13).

In brief, mannitol dimethacrylate (MDM) monomer was generated by esterifying mannitol through the reaction with acryloyl chloride. Later, the PMGT was prepared by reacting the MDM with branched polyethylenimine (bPEI, 1.2 kDa) through a Michael addition reaction.

Experiments comparing between various properties of the prepared PMGT and the PdXYP of the present invention were conducted.

6-2. Particle Size of PMGT/DNA and PdXYP Polyplex

The PdXYP of the present invention or the PMGT prepared in the Example 6-1 was conjugated to DNA to generate polyplex, and each particle size was measured. Although the particle sizes of the PdXYP/DNA polyplexes and PMGT/DNA polylexes were significantly varied, the particles of the PdXYP/DNA polyplexes were smaller than the PMGT/DNA polyplex. This is due to the fact that cohesiveness for nucleic acids of the PdXYP becomes stronger as more hydroxyl groups are present in the PdXYP.

6-3. Transfection Efficiency Measurement of PdXYP and PMGT

The transfection efficiency was compared by producing the polyplex by conjugating the PdXYP or PMGT with GFP-expressing vector (tGFP) and then treating the cells with the polyplex.

Specifically, the cells were treated with the polyplexes and after about 48 hours, the transfection efficiency of the PdXYP and PMGT was measured by confirming the GFP expression with FACS.

Figure 14:
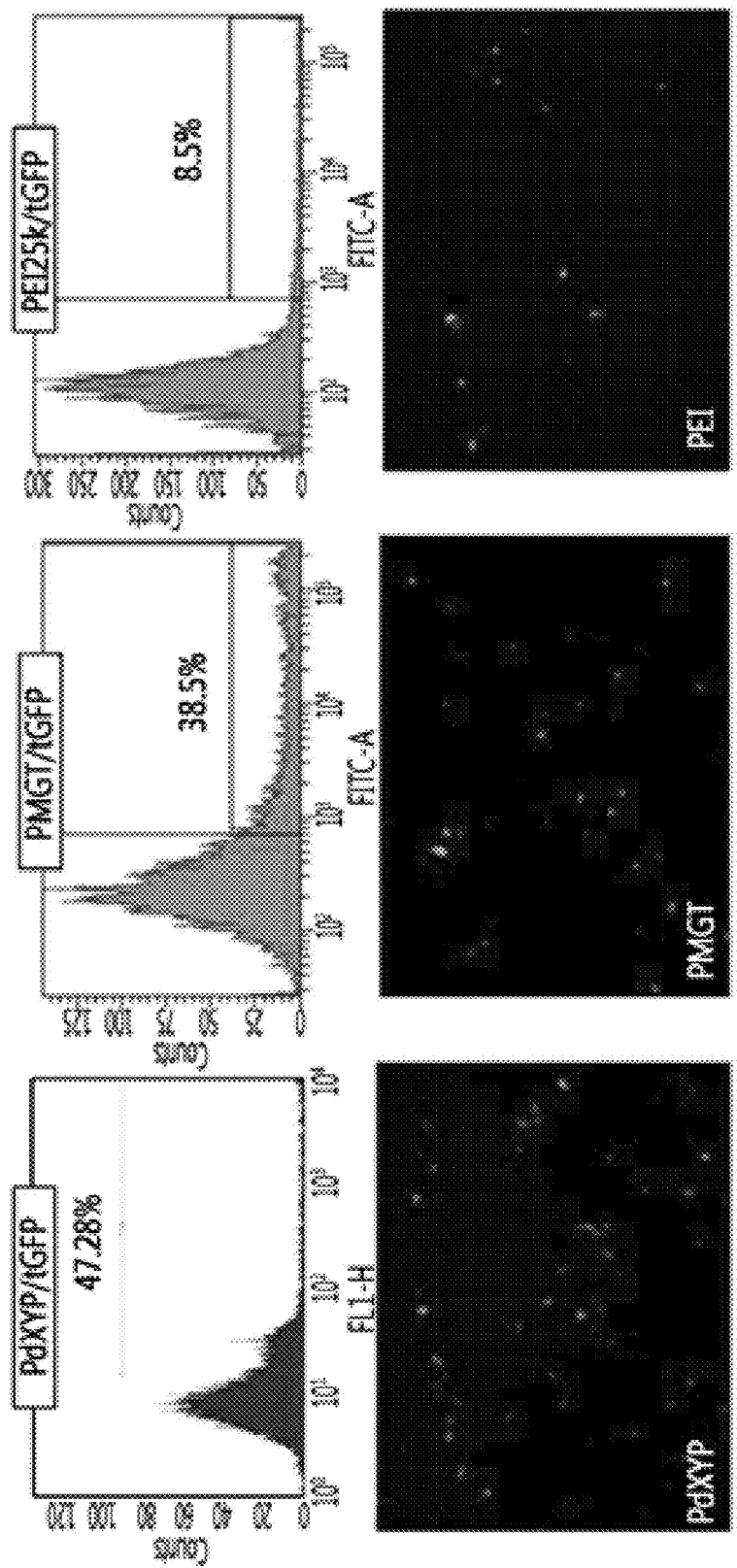
FIG. 14 shows transfection efficiency of the PdXYP, the PMGT, and the PEI by FACS.

As a result, as indicated in FIG. 14, the transfection efficiency was 38.2% in the case of the PMGT/tGFP, whereas the transfection efficiency was 47.8% in the case of the PdXYP/tGFP. Further, as indicated in FIG. 14, the cell distributions with high GFP fluorescence strength were considerably high in the case of PdXYP/tGFP.

6-4. Measurement of Osmotic Pressure

Firstly, osmotic pressure was measured in mOsm from calculating the freezing point depression of the aqueous solutions of mannitol, MDM, PEI, PMGT, and DNA polyplex at various concentrations (2%, 3%, 5%, and 10%).

The result is shown in Table 1 below.

TABLE 1

| | Osmotic Pressure [mOsm] | | | | |
|---|---|---|---|---|---|
| Conc. | Mannitol | Mannitol dimethacrylate (MDM) | PMGT | PEI 1.2 kDa | PMGT/DNA polyplex (N/P 20) | PEI/DNA polyplex (N/P 20) |
| 2% | 144 | 61 | 69 | 0 | 70 | 8 |
| 3% | 267 | 104 | 111 | 14 | 101 | 26 |
| 5% | 391 | 142 | 151 | 25 | 139 | 33 |
| 10% | 788 | 299 | 332 | 56 | 273 | 65 |

Then, osmotic pressure was measured in mOsm by calculating the freezing point depression of the aqueous solutions of xylitol, dixylitol, PdXYA, PEI, PdXYP, and DNA polyplex at various concentrations (2%, 3%, 5%, and 10%).

The result is shown in Table 2 below.

TABLE 2

| | Osmotic Pressure [mOsm] | | | | |
|---|---|---|---|---|---|
| Conc. | Xylitol | Dixylitol diacrylate (PdXYA) | PdXYP | PEI 1.2 kDa | PdXYP/DNA polyplex (N/P 20) | PEI/DNA polyplex (N/P 20) |
| 2% | 132 | 135 | 177 | 0 | 156 | 8 |
| 3% | 235 | 282 | 319 | 14 | 321 | 26 |
| 5% | 340 | 545 | 623 | 25 | 590 | 33 |
| 10% | 677 | 876 | 899 | 56 | 802 | 65 |

As indicated in Tables 1 and 2, osmotic pressure was significantly high when the PdXYP of the present invention was used, compared to PEI, PMGT, etc., which are existing gene transporters. Accordingly, an excellent cell membrane absorption ratio can be predicted because of high osmotic pressure when using the PdXYP of the present invention.

6-5. Comparison of Cellular Uptake Mechanism

Differences in cellular uptake mechanism of the PMGT and PdXYP were confirmed. When the A549 cells were treated with PMGT, COX-2 expression became higher, whereas caveolin-1 expression became higher when treated with PdXYP.

Example 7: Vitamin B6 Conjugated Polydixylitol Polymer Based Gene Transporter (VB-PdXYP)

The present inventors have prepared the gene transporter in which the PdXYP is conjugated with vitamin B6. VB6, which is a coenzyme acting on various cell metabolism including DNA biosynthesis required for growth or proliferation of cells, goes through facilitated diffusion by VB6 transporting membrane carrier (VTC) present in the cell membrane, resulting in influx of the gene transporters. Specifically, as the growth and proliferation of the cells actively occur in cancer cells, the cancer cells have the characteristic of demanding a high volume of vitamin B6, compared to general adult cells.

The VB-PdXYP of the present invention are induced to adhere to the cell membrane by binding to VTC in the cell membrane through vitamin B6. After being bound to the cell membrane, intracellular nucleic acid influx is effectively induced owing to the proton sponge effect caused by the PdXYP, thus indicating considerably improved transfection efficiency. Further, due to very low cytotoxicity, it may be effectively used as a gene transporter for gene therapy. Specifically, high transfection efficiency may be exhibited in cancer cells having high demands for vitamin B6, compared to normal cells.

Accordingly, the present inventors have prepared the VB-PdXYP through animal studies to confirm the effect thereof.

Example 8: Preparation of VB-PdXYP and Confirmation of In Vitro Effects 10 mol-% of the primary amine present in the PdXYP was reacted with vitamin B6 (pyridoxal 5' phosphate, PLP, $VB_6$) to form transient Schiff base. Later, the VB-PdXYP was obtained by reduction using $NaCNBH_4$ (FIG. 2).

Specifically, at room temperature, 10 mL of $VB_6$ (25 mg/mL) in an aqueous solution was added dropwise to 50 mL of aqueous solution where PdXYP (1 g) and $NaHCO_3$ (100 mg) were dissolved, and stirred vigorously for 24 hours. Later, $NaCNBH_4$ (50 mg) was added to reduce the Schiff base to secondary amine. The reacted mixed solution was dialyzed using a Spectra/Por membrane (MW cutoff 3.5 k; Spectrum Medical Industries, Inc., Los Angeles, Calif., USA) for 24 hours at 4° C. against distilled water. Finally, the solution was lyophilized under reduced pressure and stored at −20° C. prior to use.

Figure 15:
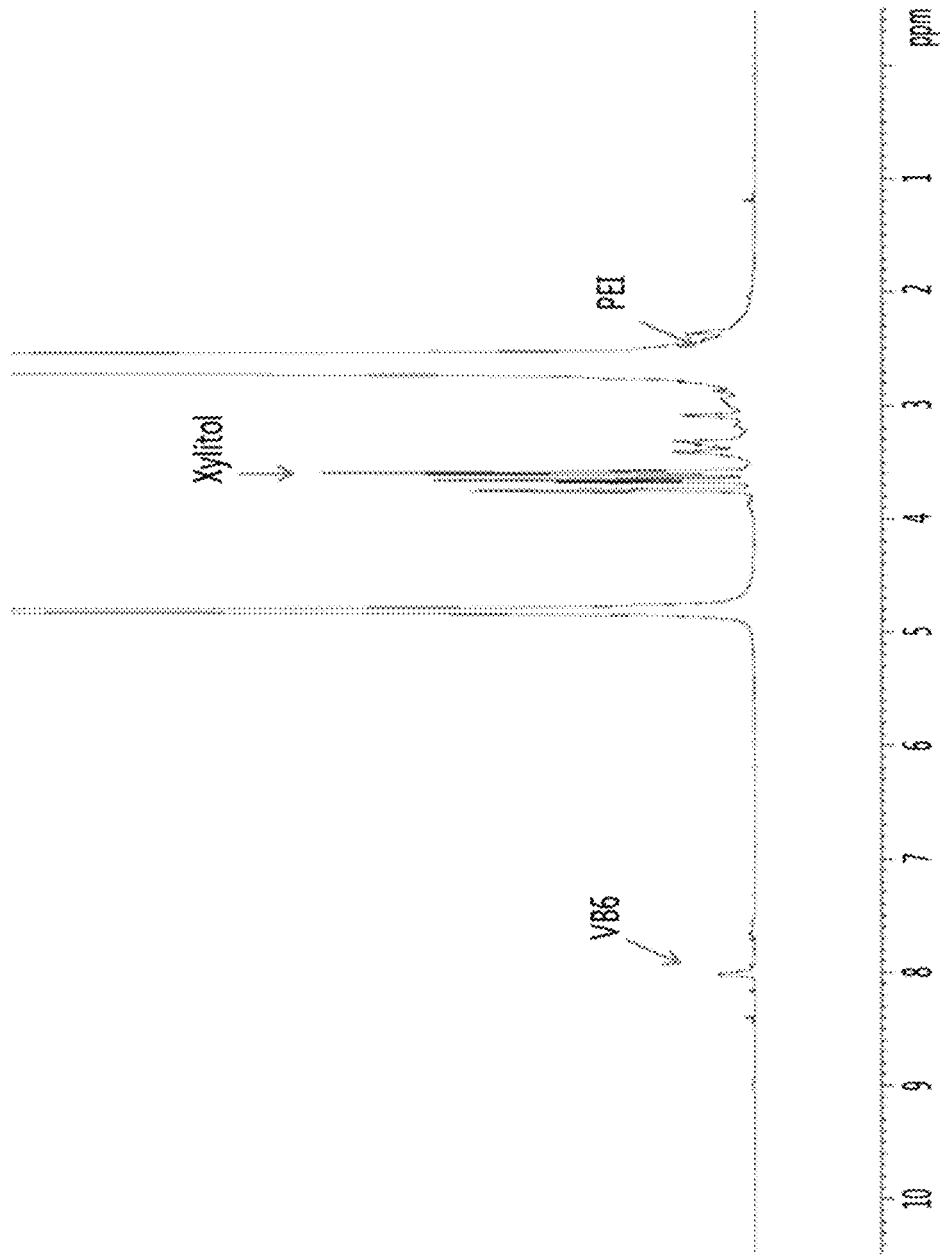
FIG. 15 shows that the VB-PdXYP was prepared by $^1$H NMR.

$^1$H NMR confirmed that the thus-obtained VB-PdXYP was prepared (FIG. 15).

The present inventors have compared the buffering effects of the prepared VB-PdXYP and PdXYP with the PEI. As a result, as indicated in FIG. 16, it was confirmed that the buffering capacity of the VB-PdXYP and the PdXYP was exceptional compared to the PEI, and specifically that the buffering capacity of the VB-PdXYP was remarkable.

The present inventors have confirmed the gene delivery efficiency of the prepared VB-PdXYP and the PdXYP in various cell lines.

As a result, it was confirmed that the VB-PdXYP and the PdXYP had superior gene delivery capacity compared to the existing gene transporters (lipofectamine), and specifically that the gene delivery capacity of the VB-PdXYP was remarkable in various cell lines, especially in cancer cell lines (FIG. 17).

Example 9: Experiment on In Vivo Effect of VB-PdXYP

Nextly, the present inventors have tried to confirm the in vivo gene delivery effect of the VB-PdXYP prepared above, especially cancer treating effects by delivering siRNA which has anticancer effects.

Firstly, 6-week old nude Balb/c mice (male, 4 mice/group) were subcutaneously injected with 100 μL of suspension containing 3×10$^6$ of A549 (PerkinElmer, Mass., USA) single cells expressing luciferase.

A month after the subcutaneous injection, tumor therapy started through siSHMT1 delivery using the VB-PdXYP of the present invention when the size of tumor, which was formed after the A549 cells have grown adhered in the tissues in the subject, reached 800×1000 mm$^3$.

100 μL of general saline solution with dissolved VB-PdXYP/siSHMT1 (30 mg) complex (N/P 20) was directly injected to the tumor at 48-hour interval for 1 month. The PdXYP/siSHMT1 complex (N/P 20), which was prepared under the same condition, was used as a control and saline solution was used as a negative control. The bioimage for tumor was obtained to measure the treatment effects for the tumor size, using the IVIS imaging system 100 (Xenogen) with Living Image software.

For this, the mice were anesthetized by intraperitoneal injection by diluting the mixed solution of zoletil (40 mg/kg):rompun (10 mg/kg) (4:1) by 8 times in sterilized 1×PBS. 200 μL of D-luciferin (15 mg/mL stock in DPBS) for 20 g mouse (3 mg per mouse) was injected intraperitoneally, which quickly distributed throughout the body. Luciferase expressed in A549 cell-derived tumors reacted with the injected luciferin to emit luminescence, and therefore, the luminescence level was captured by the IVIS system, and its level, which was proportional to the tumor size, was confirmed by an image. The measured image was obtained from a stabilized luminescence phase, which usually occurs 15 minutes after the injection with luciferin and lasts for 15 minutes to 20 minutes. Further, the tumor size was measured using a vernier caliper every week during the treatment period. The tumor size was measured with an average diameter (particle size and diameter) and the equation, m=0.5×a×b$^2$, was used (a and b are relatively the smallest diameter and the largest diameter, respectively).

Figure 18:
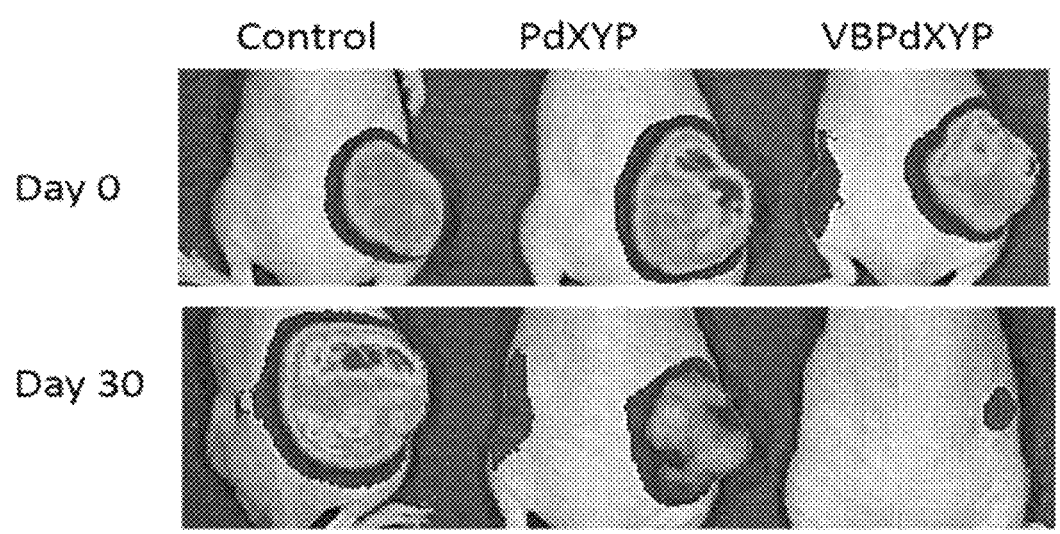
FIG. 18 shows bioluminescence images in which the anticancer effects through the gene delivery of the VB-PdXYP and the PdXYP were confirmed by measuring the tumor size in animal models transplanted with cancer.
Figure 19:
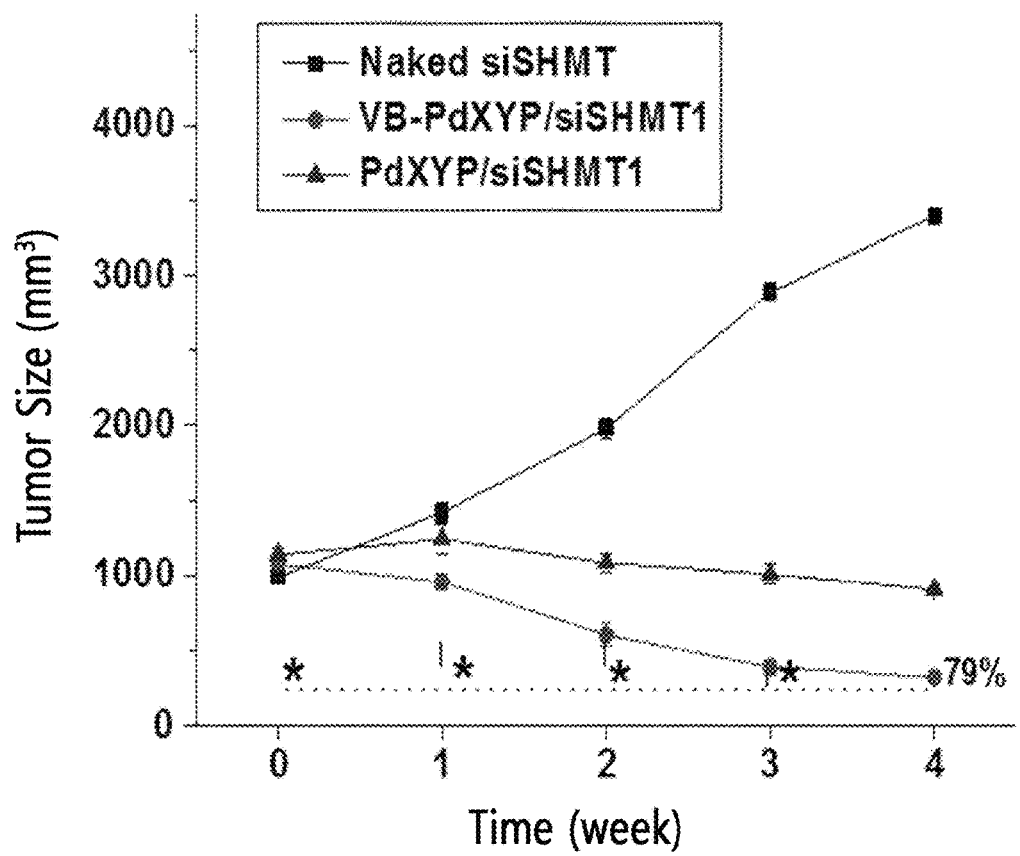
FIG. 19 shows the graph displaying the tumor size measured by the bioluminescence image regarding the anticancer effects by the gene delivery of the VB-PdXYP and the PdXYP in animal models transplanted with cancer.

A bioluminescence images was obtained a month after the polyplex injection, and the decrease in the tumor size (79% decrease of the entire tumor) of the group treated with VB-PdXYP/siSHMT1 and the inhibiting effect on tumor growth were confirmed through the measurement of bioluminescence level. In contrast, the tumor of the negative control was enlarged by a few times compared to the initial tumor size. Further, for the control treated with PdXYP/siSHMT1, an inhibition of tumor growth was successful since the tumor size did not increase, but the decreasing effect of the tumor size was not confirmed to be effective compared to the experimental group treated with VB-PdXYP/siSHMT1 (FIGS. 18 and 19).

Taken together, strong results suggesting an in vivo application of the gene transporter of the present invention have been observed. It was confirmed that the gene transporter of the present invention condensed pDNA into smaller particle size (100 nm) that has no physiological interaction with protein and aggregation due to sparse presence of positive electric charge. In comparison with the commercial gene transporters, high transfection efficiency was observed by selective stimulus of the endocytotic pathway. Further, a capacity to deliver genes transmigrating the BBB without any damages in vitro and in vivo was confirmed. In addition, as a result of preparing the gene transporter in which the PdXYP of the present invention was conjugated with vitamin B6, it was confirmed that the gene transporter may have excellent buffering effects and gene delivery capacity, especially excellent anticancer effects, when the genes were effectively delivered to cancer cells, which in turn, led to the delivery of the nucleic acids for anticancer.

What is claimed is:

1. A polydixylitol polymer-based gene transporter (PdXYP) represented by the following Formula 1:

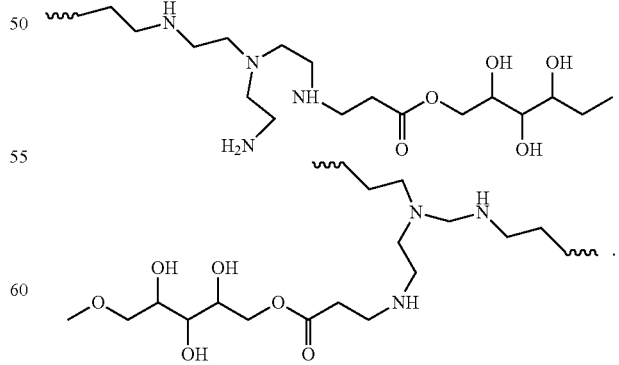

Formula 1

2. The PdXYP of claim 1, wherein the PdXYP is further conjugated to vitamin B6 and represented by the following Formula 4:

Formula 4

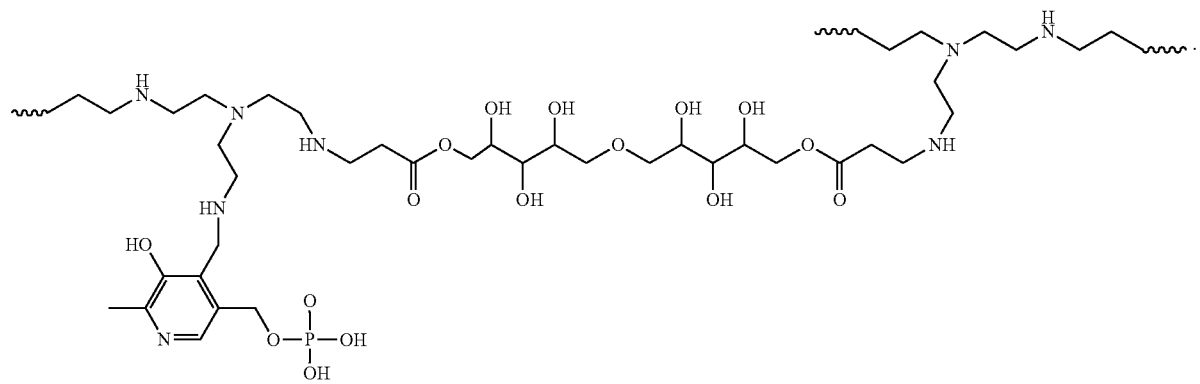

3. The PdXYP of claim 1, wherein the PdXYP is characterized in transmigrating the blood brain barrier (BBB).

4. A nucleic acid delivery complex, wherein the nucleic acids are conjugated to the PdXYP of claim 1.

5. The nucleic acid delivery complex of claim 4, wherein the nucleic acid and the PdXYP are conjugated at a molar ratio of 1:0.5 to 1:100.

6. The nucleic acid delivery complex of claim 4, wherein the nucleic acid delivery complex has an average particle size ranging from 50 nm to 150 nm.

7. The nucleic acid delivery complex of claim 4, wherein the nucleic acid delivery complex has a zeta potential ranging from 25 mV to 40 mV.

8. The nucleic acid delivery complex of claim 4, wherein the nucleic acids are selected from the group consisting of small interfering RNA (siRNA), small hairpin RNA (shRNA), endoribonuclease-prepared siRNAs (esiRNA), antisense oligonucleotides, DNA, single-stranded RNA (ss RNA), double-stranded RNA (ds RNA), DNA-RNA hybrids, and ribozymes.

9. The nucleic acid delivery complex of claim 8 wherein the nucleic acids is esiRNA of human SHMT1 capable of inhibiting serine hydroxymethyltransferase (SHMT1) expression.

10. A pharmaceutical composition for gene therapy comprising the nucleic acid delivery complex of claim 9 as an active ingredient.

11. The composition of claim 10, wherein the nucleic acid delivery complex is formulated for inhalatable or injectable administration.

12. The composition of claim 11, wherein the composition is for use in the treatment of cancer.

13. The composition of claim 12, wherein the cancer is selected from the group consisting of lung cancer, bone cancer, pancreatic cancer, skin cancer, head and neck cancer, skin melanoma, uterine cancer, ovarian cancer, rectal cancer, colorectal cancer, colon cancer, breast cancer, uterine sarcoma, fallopian tube carcinoma, endometrium carcinoma, cervix carcinoma, vagina carcinoma, vulva carcinoma, esophageal cancer, small intestine cancer, thyroid cancer, parathyroid cancer, soft tissue sarcoma, urethral cancer, penile cancer, prostate cancer, chronic or acute leukemia, pediatric solid tumor, differentiated lymphoma, bladder cancer, kidney cancer, renal cell carcinoma, renal pelvic carcinoma, primary central nervous system lymphoma, myelencephalon tumor, brain stem glioma, and pituitary gland adenoma.

14. A method for preparing polydixylitol polymer-based gene transporter (PdXYP) of claim 1, comprising:
a) preparing dixylitol by an acetone/xylitol condensation using xylitol and acetone;
b) preparing dixylitol diacrylate (dXYA) by esterifying dixylitol prepared in step a) with acryloyl chloride; and
c) obtaining PdXYP by performing a Michael addition reaction between dXYA prepared in step b) and a low-molecular weight polyethyleneimine (PEI).

15. The method of claim 14, wherein the low-molecular weight PEI has a weight-average molecular weight ranging from 50 Da to 10,000 Da.

16. The method of claim 14, wherein the low-molecular weight PEI is branched-type.

17. The method of claim 14, the Michael addition reaction in step c) is performed for 1 hour to 72 hours at 40° C. to 100° C.

18. The method of claim 14, further comprising:
d) conjugating vitamin B6 to the PdXYP prepared in step c).

* * * * *